United States Patent
Saragovi et al.

(10) Patent No.: US 6,881,719 B2
(45) Date of Patent: Apr. 19, 2005

(54) β-TURN PEPTIDOMIMETIC CYCLIC COMPOUNDS

(75) Inventors: Horacio Uri Saragovi, Westmount (CA); Kevin Burgess, Bryan, TX (US)

(73) Assignees: McGill University (CA); The Texas A&M University System, College Station, TX (US)

( * ) Notice: Subject to any disclaimer, the term of this patent is extended or adjusted under 35 U.S.C. 154(b) by 2 days.

(21) Appl. No.: 10/181,546

(22) PCT Filed: Jan. 18, 2001

(86) PCT No.: PCT/CA01/00043
§ 371 (c)(1),
(2), (4) Date: Nov. 18, 2002

(87) PCT Pub. No.: WO01/52843
PCT Pub. Date: Jul. 26, 2001

(65) Prior Publication Data
US 2003/0211982 A1 Nov. 13, 2003

Related U.S. Application Data
(60) Provisional application No. 60/176,482, filed on Jan. 18, 2000.

(51) Int. Cl.$^7$ .......................... A61K 38/06; A61K 38/07
(52) U.S. Cl. .......................... 514/11; 530/330; 530/331
(58) Field of Search .............................. 514/9, 10, 11; 530/317, 321, 330, 331

(56) References Cited

U.S. PATENT DOCUMENTS 5,034,224 A * 7/1991 Kantor et al. ................ 424/122
5,411,948 A * 5/1995 Lingwood et al. ............ 514/78

FOREIGN PATENT DOCUMENTS

WO   WO 95/21193 A1 * 8/1995

OTHER PUBLICATIONS

"Confirmations of Peptidomimetics Formed by SNAr Macrocyclizations: 13– to 16–Membered Ring Systems", By Zhicheng Wang et al., Chem. Eur. Journal 1999, 5, No. 11, pp. 3273–3276.
"Stereochemical Implications on Diversity in β–Turn Peptidomimetic Libraries", By Yangbo Feng et al., Journal Org. Chem. 1999, 64, pp. 9175–9177.
"SNAr Cyclizations to Form Cyclic Peptidomimetics of β–Turns", By Yangbo Feng et al., Am. Chem. Soc. 1998, 120, pp. 10768–10769.
"Solid–Phase SNAr Macrocyclizations to Give Turn–Extended–Turn Peptidomimetics", By Yangbo Feng et al., Chem. Eur. Journal, 1999, 5, No. 11, pp. 3261–3272.
"Resin Effects in Solid Phase SNAr and SN2 Macrocyclizations", By Yangbo Feng et al., Biotechnology and Bioengineering (Combinatorial Chemistry), vol. 71, No. 1, Winter, 2000, pp. 1–8.
"A Designed Peptidomimetic Agonistic Ligand of TrkA Nerve Growth Factor Receptors", By Sergei Maliartchouk et al., Mol. Pharmacol. 2000, vol. 57, No. 2, pp. 385–391.

* cited by examiner

*Primary Examiner*—Jeffrey Edwin Russel
(74) *Attorney, Agent, or Firm*—Bachman & LaPointe, P.C.

(57) ABSTRACT

Proteolytically stable small molecule β-turn peptidomimetic compounds have been identified as agonists or antagonists of neurotrophin receptors, such as TrkA. A compound of particular interest binds the immunoglobulin-like C2 region of the extracellular domain of TrkA, competes the binding of another TrkA ligand, affords selective trophic protection to TrkA-expressing cell lines and neuronal primary cultures, and induces the differentiation of primary neuronal cultures. The small β-turn peptidomimetic compounds of the invention can activate a tyrosine kinase neurotrophin receptor that normally binds a relatively large protein ligand. Such compounds that bind the extracellular domain of Trk receptors are useful pharmacological agents to address disorders where Trk receptors play a role, by targeting populations selectively.

16 Claims, 3 Drawing Sheets

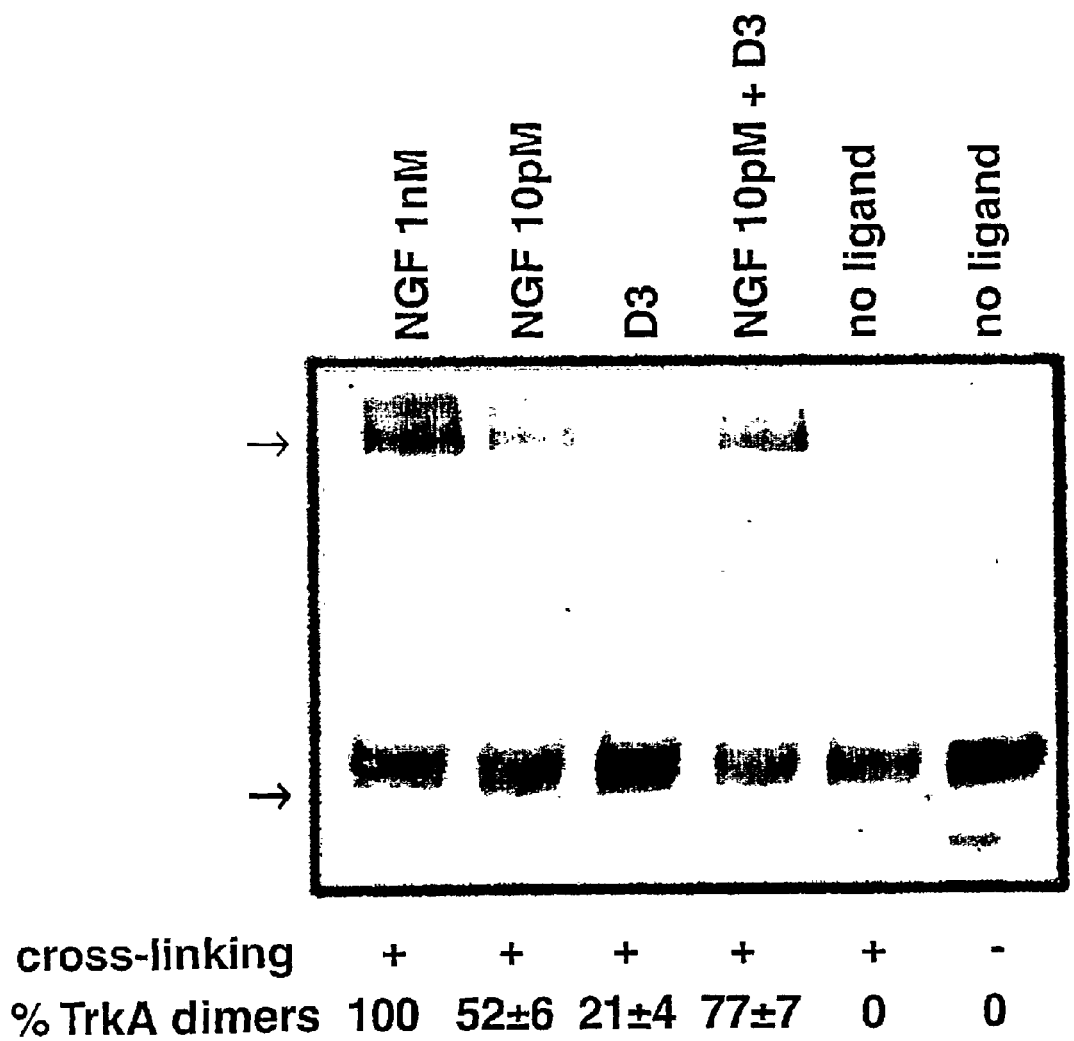

SEQUENCE LISTING

<160> NUMBER OF SEQ ID NOS: 16

<210> SEQ ID NO 1
<211> LENGTH: 8
<212> TYPE: PRT
<213> ORGANISM: M. musculus or R. rattus

<400> SEQUENCE: 1

Ser Ser Thr His Pro Val Phe His
 1               5

-continued

```
<210> SEQ ID NO 2
<211> LENGTH: 11
<212> TYPE: PRT
<213> ORGANISM: M. musculus or R. rattus

<400> SEQUENCE: 2

Thr Ala Thr Asp Ile Lys Gly Lys Glu Val Thr
 1               5                  10

<210> SEQ ID NO 3
<211> LENGTH: 8
<212> TYPE: PRT
<213> ORGANISM: H. sapiens

<400> SEQUENCE: 3

Ser Ser Ser His Pro Ile Phe His
 1               5

<210> SEQ ID NO 4
<211> LENGTH: 11
<212> TYPE: PRT
<213> ORGANISM: H. sapiens

<400> SEQUENCE: 4

Thr Ala Thr Asp Ile Lys Gly Lys Glu Val Met
 1               5                  10

<210> SEQ ID NO 5
<211> LENGTH: 7
<212> TYPE: PRT
<213> ORGANISM: R. rattus or H. sapiens

<400> SEQUENCE: 5

Tyr Ala Glu His Lys Ser His
 1               5

<210> SEQ ID NO 6
<211> LENGTH: 11
<212> TYPE: PRT
<213> ORGANISM: R. rattus or H. sapiens

<400> SEQUENCE: 6

Ser Ala Ile Asp Ile Arg Gly His Gln Val Thr
 1               5                  10

<210> SEQ ID NO 7
<211> LENGTH: 9
<212> TYPE: PRT
<213> ORGANISM: H. sapiens

<400> SEQUENCE: 7

His Ser Asp Pro Ala Arg Arg Gly Glu
 1               5

<210> SEQ ID NO 8
<211> LENGTH: 11
<212> TYPE: PRT
<213> ORGANISM: H. sapiens

<400> SEQUENCE: 8

Thr Ala Val Asp Met Ser Gly Gly Thr His Ser
 1               5                  10
```

```
<210> SEQ ID NO 9
<211> LENGTH: 9
<212> TYPE: PRT
<213> ORGANISM: R. rattus or H. sapiens

<400> SEQUENCE: 9

Glu Val Asn Ile Asn Asn Ser Val Phe
 1               5

<210> SEQ ID NO 10
<211> LENGTH: 14
<212> TYPE: PRT
<213> ORGANISM: M. musculus

<400> SEQUENCE: 10

Arg Gln Leu Thr Thr Asp Glu Lys Gln Ala Ala Trp Arg Phe
 1               5                  10

<210> SEQ ID NO 11
<211> LENGTH: 14
<212> TYPE: PRT
<213> ORGANISM: R. rattus

<400> SEQUENCE: 11

Lys Gln Leu Thr Thr Asp Asp Lys Gln Ala Ala Trp Arg Phe
 1               5                  10

<210> SEQ ID NO 12
<211> LENGTH: 14
<212> TYPE: PRT
<213> ORGANISM: H. sapiens

<400> SEQUENCE: 12

Lys Gln Leu Thr Met Asp Gly Lys Gln Ala Ala Trp Arg Phe
 1               5                  10

<210> SEQ ID NO 13
<211> LENGTH: 9
<212> TYPE: PRT
<213> ORGANISM: R. rattus or H. sapiens

<400> SEQUENCE: 13

Glu Ile Lys Thr Gly Asn Ser Pro Val
 1               5

<210> SEQ ID NO 14
<211> LENGTH: 15
<212> TYPE: PRT
<213> ORGANISM: R. rattus or H. sapiens

<400> SEQUENCE: 14

Lys Gln Leu Thr Ser Glu Asn Asn Lys Leu Val Gly Trp Arg Trp
 1               5                  10                  15

<210> SEQ ID NO 15
<211> LENGTH: 9
<212> TYPE: PRT
<213> ORGANISM: H. sapiens

<400> SEQUENCE: 15

Glu Lys Val Pro Val Ser Lys Gly Gln
 1               5

<210> SEQ ID NO 16
<211> LENGTH: 15
```

```
<212> TYPE: PRT
<213> ORGANISM: H. sapiens

<400> SEQUENCE: 16

Arg Ala Leu Thr Met Asp Ser Lys Lys Arg Ile Gly Trp Arg Phe
1               5                   10                  15
```

β-TURN PEPTIDOMIMETIC CYCLIC COMPOUNDS

CROSS-REFERENCE TO RELATED APPLICATIONS

This application is a U. S. national entry from International Application PCT/CA01/00043, filed Jan. 18, 2001, and claims the benefit under 35 U.S.C. 119(e) of U. S. provisional application 60/176,482, filed Jan. 18, 2000.

STATEMENT OF GOVERNMENT INTEREST

This invention was made in part with U.S. Government support under Grant No. 5RO1CA082642-03, of the National Institute of Health. The Government has certain rights in this invention.

TECHNICAL FIELD

This invention relates to β-turn peptidomimetic cyclic compounds useful in the field of neurotrophin receptor agonists and antagonists; the invention also relates to neurotrophin receptor agonist and antagonist pharmaceutical compositions; a method of treating or preventing disorders mediated or regulated by neurotrophin receptors; use of β-turn peptidomimetic cyclic compounds in evaluating structural requirements of neurotrophin receptor agonists and antagonists; identification of receptor subdomains desired for ligand docking, and novel β-turn peptidomimetic cyclic compounds.

BACKGROUND ART

Tyrosine kinase A (TrkA) is a transmembrane tyrosine kinase receptor with high selectivity for the neurotrophin nerve growth factor (NGF). Related neurotrophins include Brain Derived Neurotrophic Factor (BDNF) which binds tyrosine kinase B (TrkB) receptors, and Neurotrophin-3 (NT-3) which prefers binding to tyrosine kinase C (TrkC) receptors.

Docking of TrkA with NGF initiates receptor dimerization, catalytic phosphorylation of cytoplasmic tyrosine residues on the receptor, and a cascade of cell signaling events. These signals lead to prevention of apoptotic cell death, to promotion of cellular differentiation and axon elongation, and upregulation of choline acetyl transferase (ChAT). The same applies to other neurotrophins, except that different cell populations respond selectively based on their receptor expression patterns. NGF will be used as the proof of principle but the notions apply to all neurotrophins (NTFs).

Several neuronal cell types that are implicated in important disease states express TrkA and therefore respond to NGF, including sensory, sympathetic and cholinergic neurons. It has been suggested that NGF therapy may delay the onset of Alzheimer's disease prevent functional loss associated with cerebral stroke, and ameliorate peripheral diabetic neuropathies. Other applications proposed for NGF include treatment of neuronal damage, and targeting of neuroectoderm-derived tumors. For a review of disease targets see (Saragovi and Burgess, 1999).

Despite the therapeutic potential of NGF clinical trials featuring this protein have been disappointing (Saragovi and Burgess, 1999). There are several reasons for this: inherent drawbacks associated with the use of polypeptides applied as drugs, in vivo instability, and pleiotropic effects due to activation of signals that were not intentionally targeted. Moreover, the NGF protein is relatively expensive to produce for medicinal applications.

Agonists of TrkA, TrkB and Trk C and p75 receptor would have utility in the treatment and prevention of tyrosine kinase receptor mediated disorders, for example, chronic or acute neurodegeneration, pain, cancer, cerebral stroke, neuromas, ocular nerve diseases, such as glaucoma, and Alzheimer's disease.

Strategies that result in agonists of tyrosine kinase receptors have not been well established. Previously, ligand mimicry and antibody mimicry strategies have been attempt to generate peptide analogs of two agonists directed to the extracellular domain of TrkA: the natural ligand NGF; (LeSauteur et al, 1995), and monoclonal antibody (mAb) 5C3 (LeSauteur et al., 1996). TrkA binding is mediated by discrete β-turn regions of these ligands. Only certain cyclic β-turn analogs were active (Beglova et al., 1998), and other conformers or linear peptides were inactive.

DISCLOSURE

This invention seeks to provide a neurotrophin receptor agonist or antagonist pharmaceutical composition.

The invention also seeks to provide a method of treating or preventing disorders of tissues where neurotrophin receptors pay a role.

Still further this invention seeks to provide β-turn peptidomimetic cyclic compounds for use in evaluating structural requirements of neurotrophin receptor agonists and antagonists.

The invention also seeks to provide a novel class of β-turn peptidomimetic cyclic compounds.

In accordance with one aspect of the invention there is provided a neurotrophin receptor agonist or antagonist pharmaceutical composition comprising an acceptable neurotrophin receptor agonistic or antagonistic amount of a neurotrophin mimicking β-turn peptidomimetic cyclic compound, in association with a pharmaceutically acceptable carrier.

In accordance with another aspect of the invention there is provided a method of treating or preventing a neurotrophin receptor mediated or regulated disorder in a patient comprising administering to a patient in need, an acceptable neurotrophin receptor agonistic or antagonistic amount of a neurotrophin mimicking β-turn peptidomimetic cyclic compound.

In accordance with still another aspect of the invention there is provided use of β-turn peptidomimetic cyclic compounds in evaluating structural requirements of neurotrophin mimicking β-turn peptidomimetic cyclic compounds.

In accordance with yet another aspect of the invention there is provided a β-turn peptidomimetic cyclic compound of formula (I)

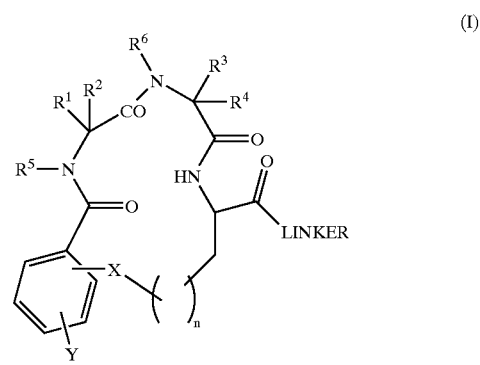

The compounds of formula (I) include the material termed D3 and derivatives thereof.

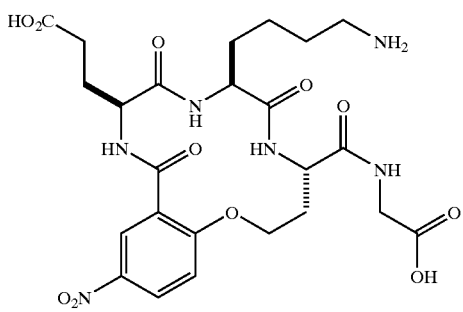

D3

D3-Biotin

Some of these derivatives may be simple and obvious modifications like biotinylated forms and molecules wherein two such units are linked by dimers. Other obvious derivatives of D3 include the following. The side chains $R^1$–$R^6$ could include any alkyl or aryl substituent found in natural and unnatural amino acids.

The side chains typical of the protein amino acids (eg Arg, Trp, His) are of particular interest, and many compounds in this series have been prepared herein, but the diversity of structures that are easily generated derivatives of D3 include many types of functional groups. The constituent amino acids may be N-alkyl, N-aryl, α,α-dialkyl, and cyclic derivatives such as might be formed from cyclopropane amino acids.

The substituent(s) Y may be hydrogen or one or two aromatic substituents for example nitro, amino, halo, alkyl for example alkyl of 1 to 6, preferably 1 to 4 carbon atoms, and aryl for example phenyl or naphthyl. The alkyl and aryl substituents Y may be unsubstituted or substituted, suitable substituents being nitro and alkyl of 1 to 6 carbon atoms.

Y may also be derivatized with a functional group, for example biotin. The group X may be any nucleophilic atom like O, N, S, P, Se, but also others such as C, or may be an alkylene radical typically of 1 to 6 carbon atoms, for example methylene; or NH. The point of connection could be ortho- or meta- to the benzoyl carbonyl. Permissible values of "n" are 0, 1, 2, 3, 4, and 5. The liking side chain that incorporates X may be aliphatic as indicated in structure (I) aromatic or heteroaromatic.

The side chain alkyl groups $R^1$, $R^2$, $R^3$, $R^4$, $R^5$, and $R^6$ can be varied in many ways to enhance the biological activities of these materials. Typically $R^1$, $R^2$, $R^3$, and $R^4$ are amino acid side-chain substituents found in the twenty protein-amino acids or side-chains very similar to these, for example the side-chains of glutamic acid, lysine, ornithine and threonine, in either enantiomeric configuration. If the $R^1$ substituent is an amino acids side chain, the other substituent on that carbon, $R^2$, will typically be hydrogen, but could also be methyl, ethyl or benzyl. Alternatively, $R^1$ and $R^2$ could be joined as in cyclopropane, cyclobutane, cyclopentane, and cyclohexane, residues. $R^3$ and $R^4$ are related in the same way as $R^1$ and $R^2$ as described above. That is, one of them will be an amino acid side chain or something very similar to this. The other of these two substituents is hydrogen in most cases, but could also be methyl, ethyl, propyl, benzyl or some simple alkyl system as described above.

There is much scope for variation in $R^5$ and $R^6$ but by far the most common substituent at these positions is hydrogen. Those substituents might also be designed to correspond to one of the side chains of the twenty protein-amino acids, notably methyl.

The compounds (I) are more especially compounds prepared from the twenty protein amino acids or simple analogs of these, including their enantiomers, N-alkyl, N-aryl, α,α-dialkyl, and cyclic amino acids. Side chains found to be particularly conducive to biological activities are $R^1$ and $R^3$ as side chains of lysine, glutamic acid, tyrosine, iso-leucine, asparagine, and threonine, $R^2$, $R^4$, $R^5$, and $R^6$ as hydrogen. One or more of the side chain are selected especially to correspond to side chains within turn regions of the neurotrophin proteins that the cyclic compound mimics, eg NGF, NT-3, NT 4/5 and/or BDNF.

In general the macrocyclic compounds have 13 to 16 membered rings where the X substituent is O, N, S, SO, or $SO_2$. The molecular fragments Z and Y are typically aromatic rings based on a simple ring system, particularly substituted benzenes. Nitro, amino, chloro, bromo, and fluoro-substituted benzenes are all permissible at this position.

Overall, several hundreds of compounds have been prepared that conform to the structure given above. Some specific examples of compounds (I) and which have been tested in assays for neurotrophin-related activities are listed below.

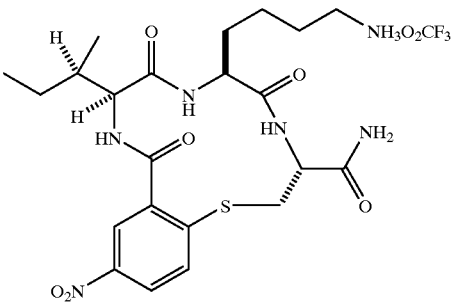

C62
(IKCys)

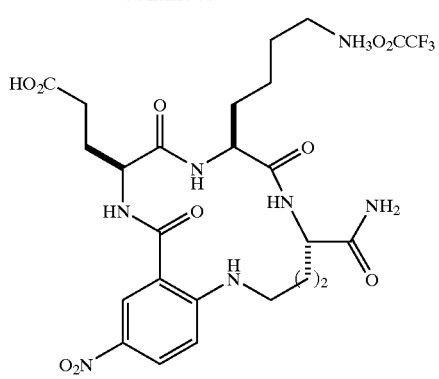
C66 or D7
(EKOm)
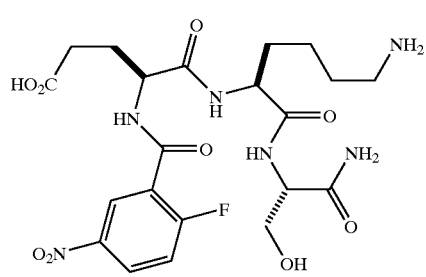
C67
(EKSer)
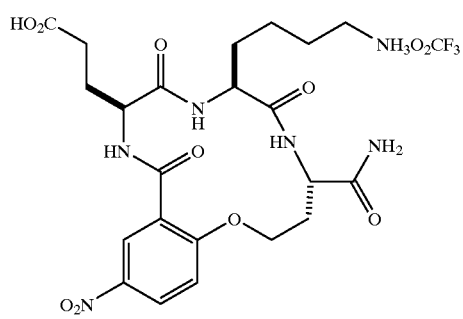
D22
(EKHse)
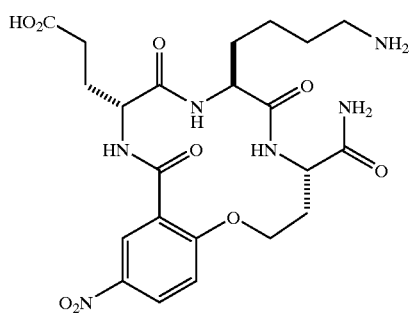
D53a
(eKHse)
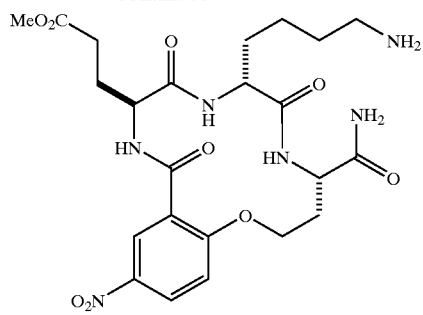
D53b–d
(EkHse)
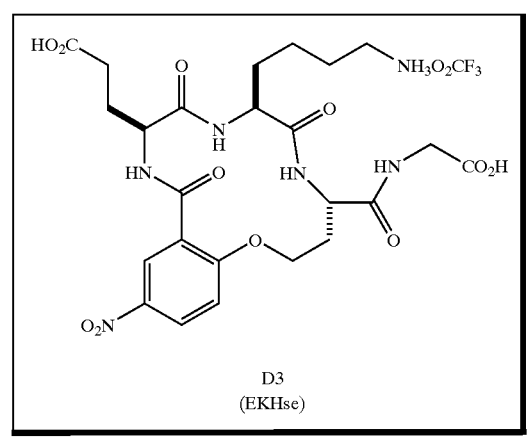
D3
(EKHse)
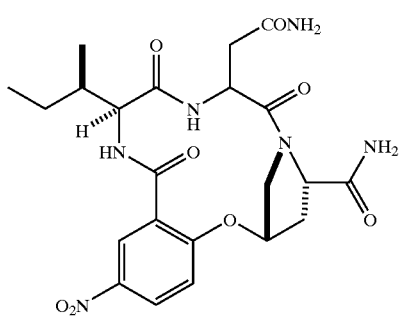
C69
(INHyp)
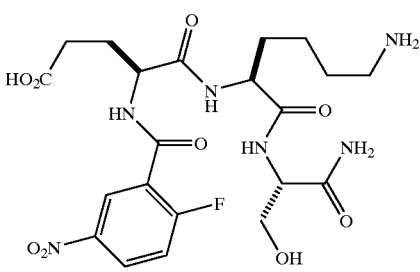
C87a
(EKSer-L)

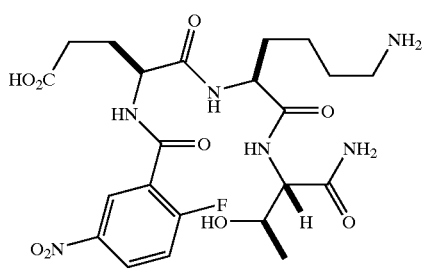
C88
(EKThr-L)
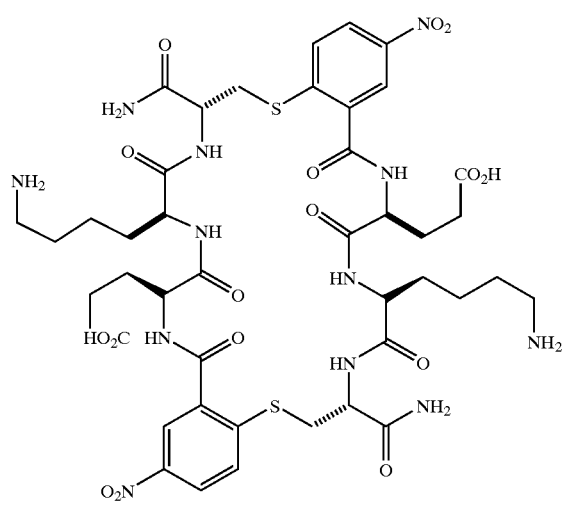
D59b
(EKCys-DI)
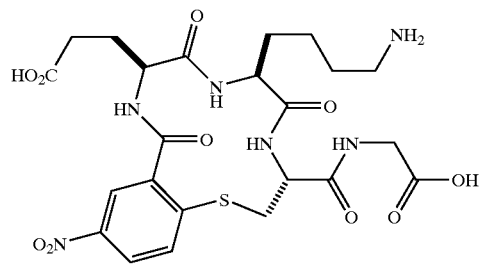
D2a
(EKCys-G)
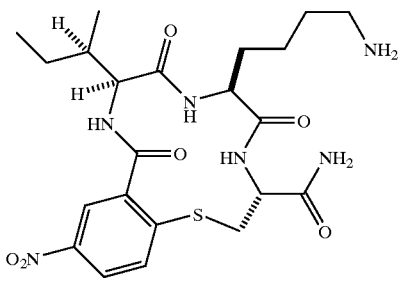
C62
(IKCys)
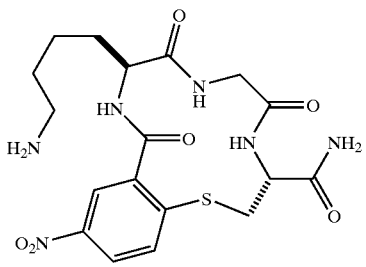
C63
(KGCys)
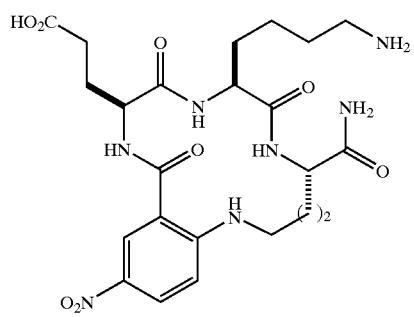
D7
(EKOrn)
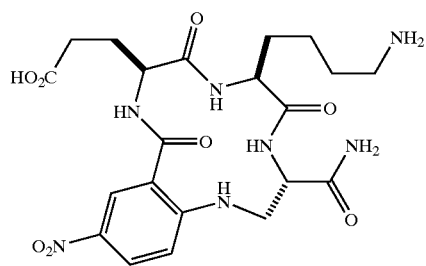
D28
(EKDpr)
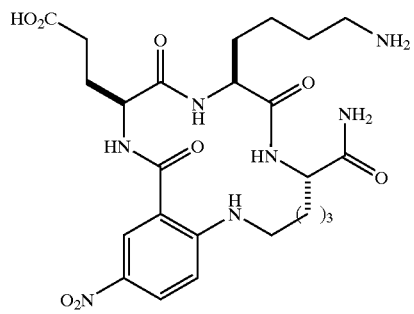
D27
(EKLys)

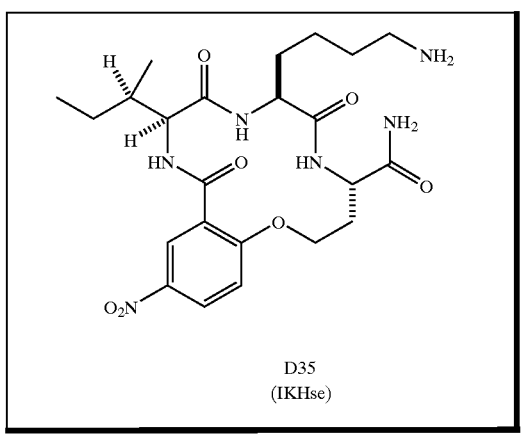
D35
(IKHse)
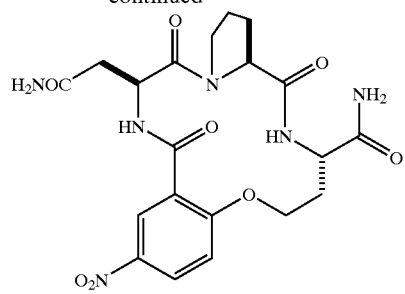
D57a
(NPHse)
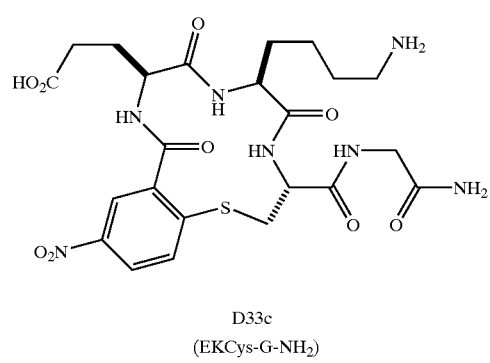
D33c
(EKCys-G-NH$_2$)
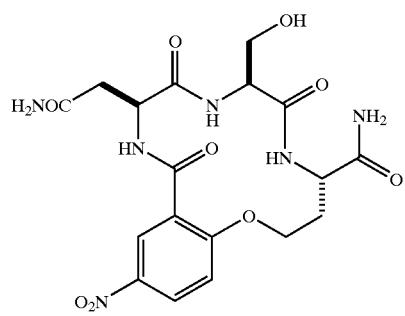
D58b
(NSHse)
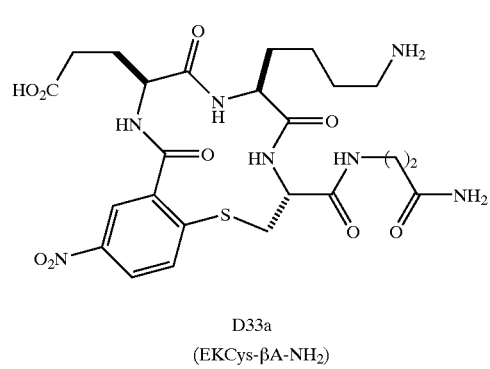
D33a
(EKCys-βA-NH$_2$)
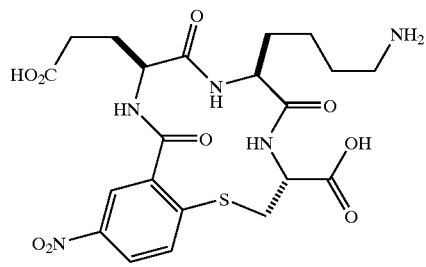
D44
(EKCys-OH)
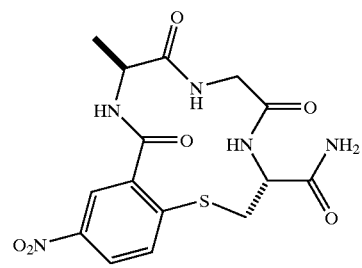
D40
(AGCys)
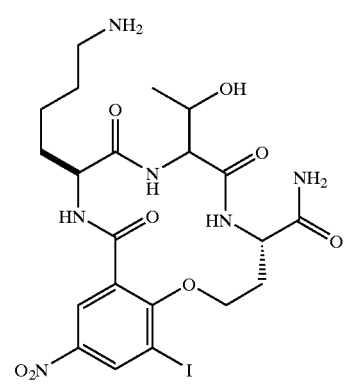
P-27, KTHse

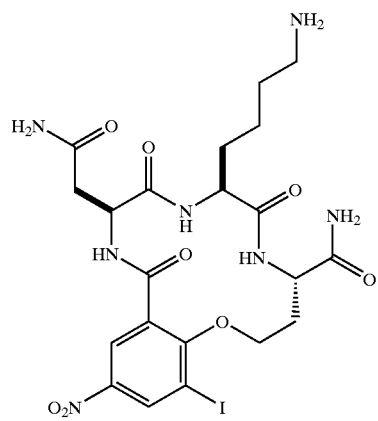
P-30, NKHse
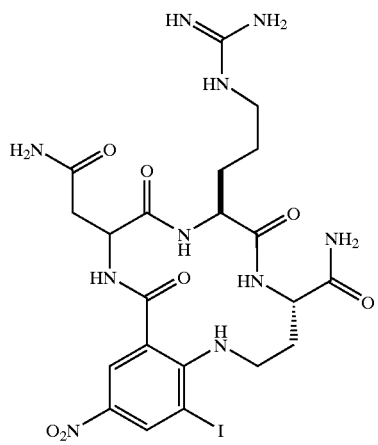
CP-5, NRBaba
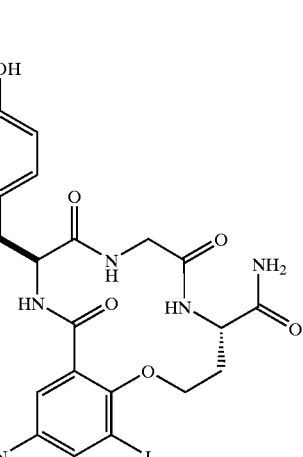
P-32, TGHse
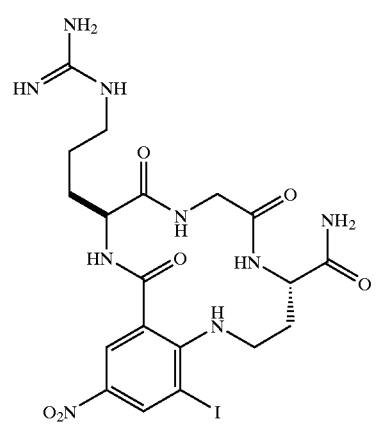
CP-6, RGBaba
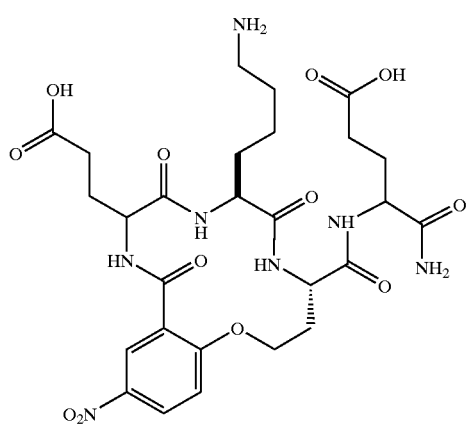
43, EKHse-E-NH2
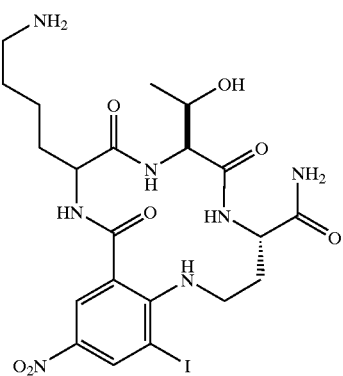
CP-7, KTBaba

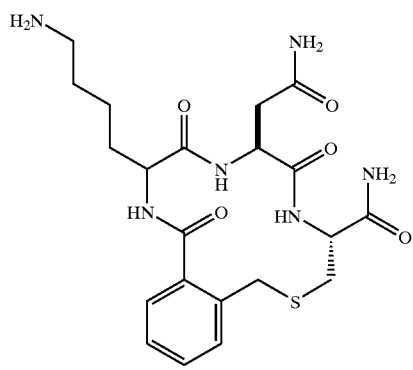
25, KNCys, YF-D87A
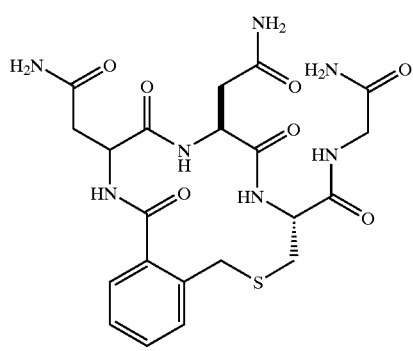
26, NNCys-G-NH2, YF-D87B
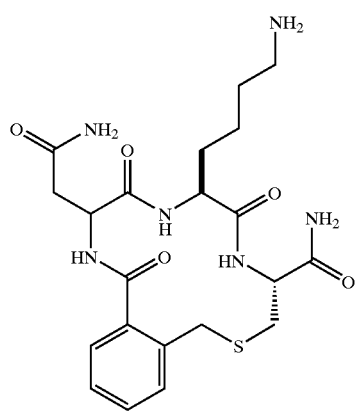
27, NKCys, YF-D87C
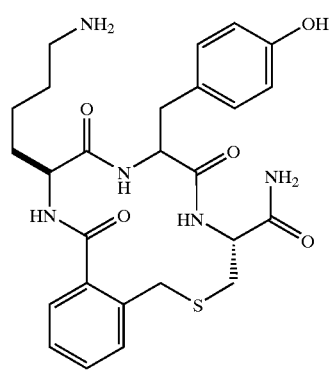
28, KYCys, YF-D88C
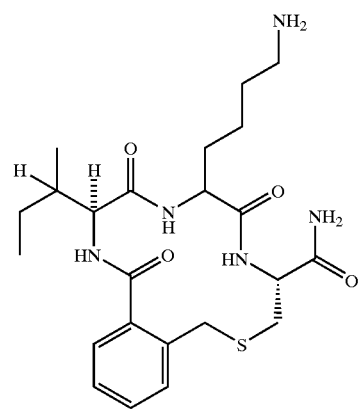
34, IKCys, YF-D84A
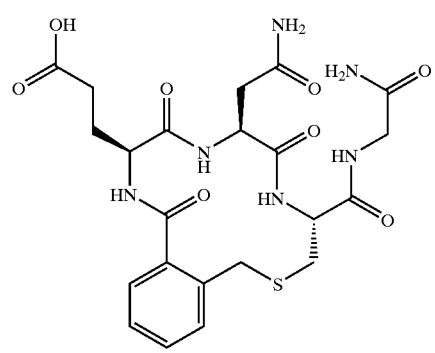
35, ENCys-G-NH2, YF-D90B
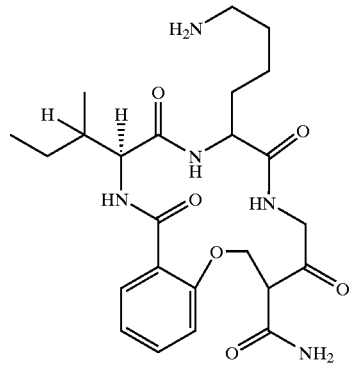
61, IKGSer, YF-E8
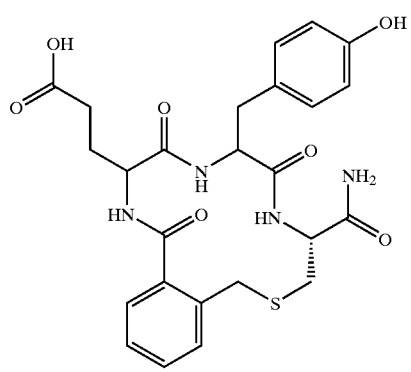
62, EYCys, YF-E6

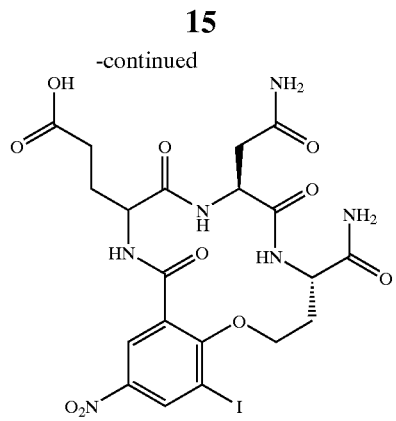
P-29, ENHse
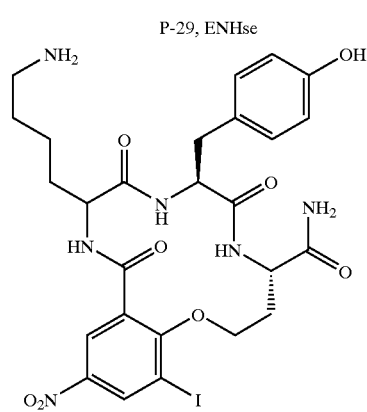
P-31, KYHse
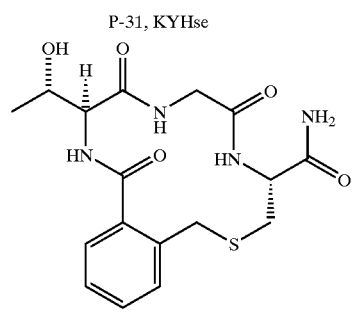
38, TGCys, YF-D91B
Examples of embodiments that mimic neurotrophic activity are agents termed D3, P27, D53b–d, 25, P56, P57, P58, P39, D21, D46, D40, and P23. Examples of embodiments that antagonize neurotrophic activity are P42 and P43. These agents are shown below:
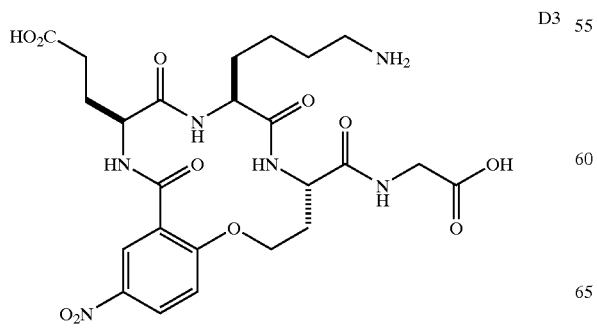
D3
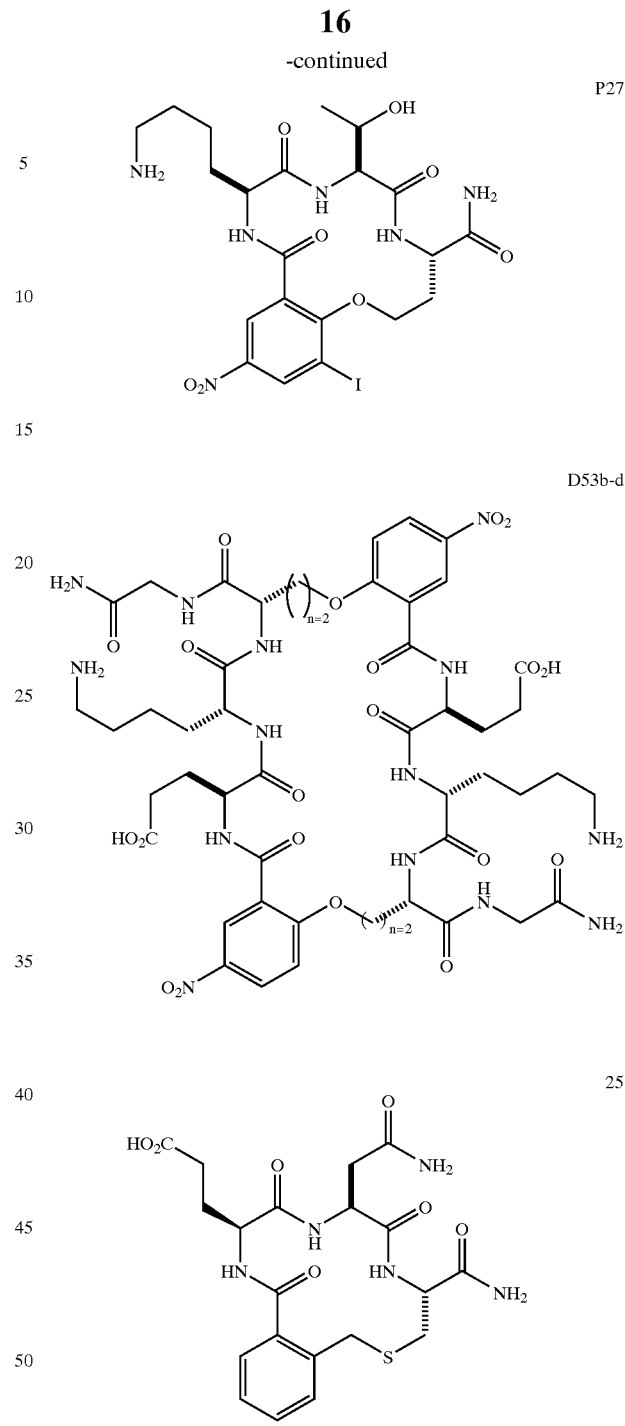
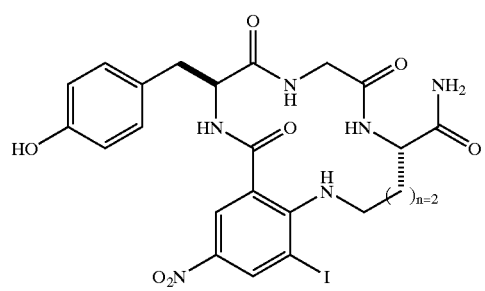
P56

P57 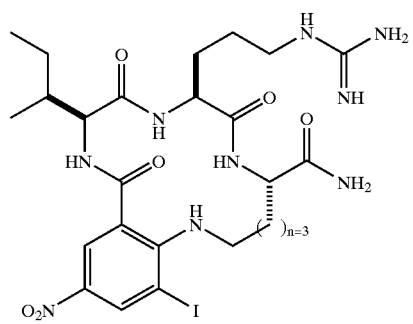

P58 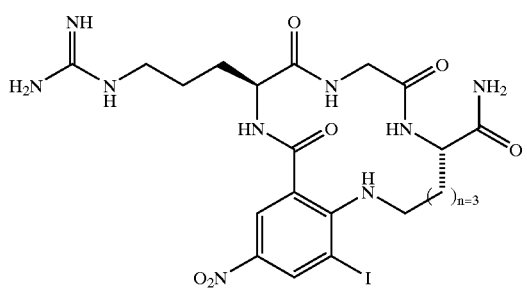

P42 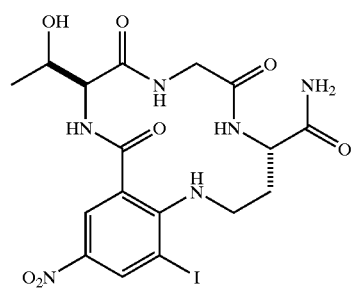

P43 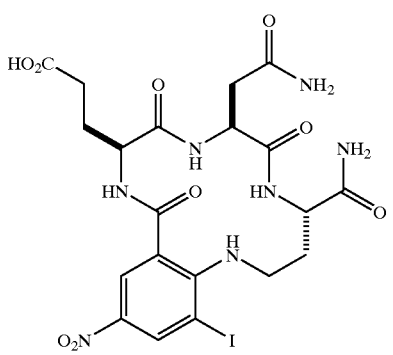

P39 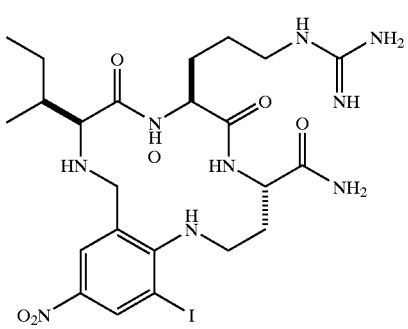

D21 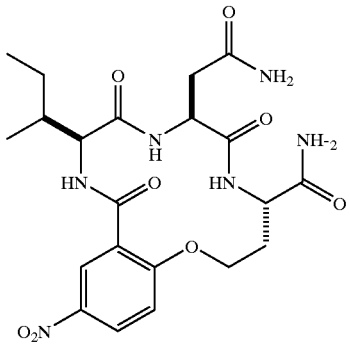

D46 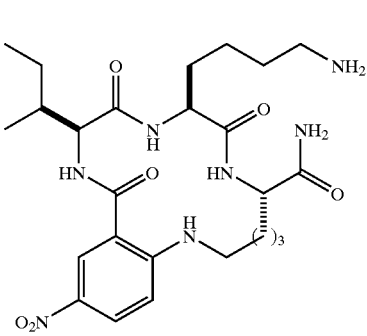

P40 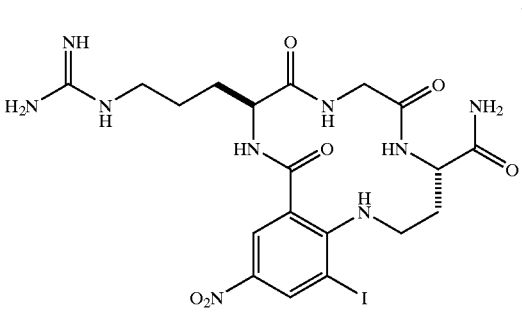

P23 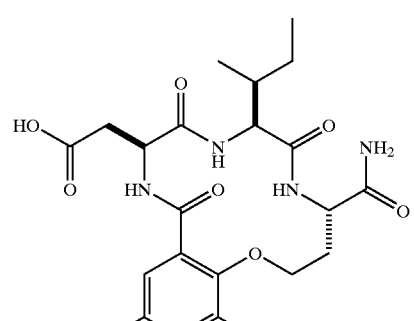

DETAILED DESCRIPTION OF INVENTION

Small, proteolytically stable molecules with neurotrophic activity, selective for cells expressing neurotrophin receptors (Trk tyrosine kinase receptors, and p75 receptors) have been developed in the present invention.

Based on the pharmacophores of the mAb 5C3 and of NGF peptide analogs described previously, a focussed library of β-turn peptidomimetic compounds has been synthesized.

This library of compounds is composed of β-turn peptidomimetic cyclic compounds. These compounds, in particular, mimic neurotrophins, and thus are agonists or antagonists for the neurotrophin receptors, or can be employed in the screening and/or evaluation of necessary structural requirements of such agonists and antagonists.

In general the cyclic compounds have a macrocyclic ring of 13 to 17, more especially 14, 15 or 16 ring atoms; and the ring is formed predominantly by a carbon and nitrogen backbone having side chains of amino acids which may be natural or synthetic.

The ring may be characterized by one or more side chains on the peptido linkage, especially at the i, i+1, i+2 and i+3 positions. The cyclic compound typically has 1, 2 or 3 side chains.

The one or more side chains more especially correspond to side chains within β-turns of a neurotrophin protein which the cyclic compound mimics, and in particular the β-turns correspond to the β-turns of a neurotrophin as NGF, NT-3, NT 4/5 and BDNF.

The β-turn peptidomimetic cyclic compounds of the invention, may, in particular embodiments be represented by the formula (I), as defined hereinbefore.

In formula (I), the macrocyclic ring containing $R_1$ to $R_6$ suitably has 13 to 17 and preferably 14, 15 or 16 ring atoms.

In preferred embodiments X is O, S or NH and R1, R3, R5 and R6 are hydrogen atoms. When Y is a substituent it may function as a label or precursor of a label, which label can be employed in the assessment of the direct binding, the in vivo distribution, and agonist or antagonist capability of the cyclic compound.

The LINKER group functions as a linking group to form dimers of the compound (I) by reaction with a homo bifunctional compound such as polyethylene glycol. Suitable LINKER groups include $NH_2$, OH, SH, COOH, $CH_3CO$ and CHO.

Representative compounds of formula (I) which have been produced as part of the afore-mentioned library are indicated hereinafter.

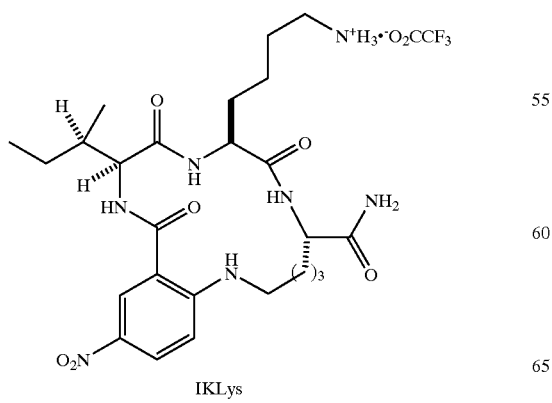

IKLys

-continued

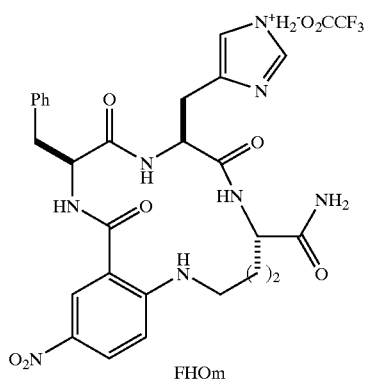

FHOm

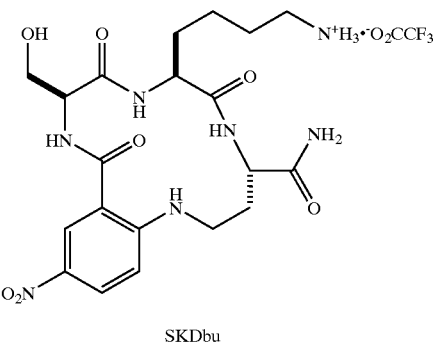

SKDbu

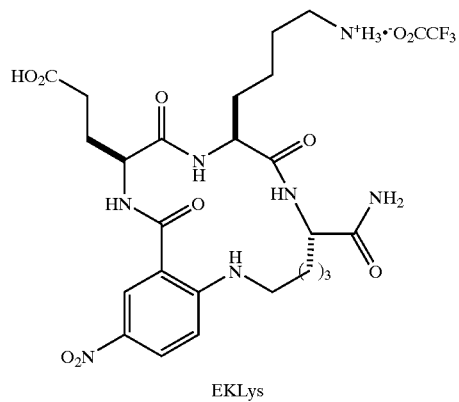

EKLys

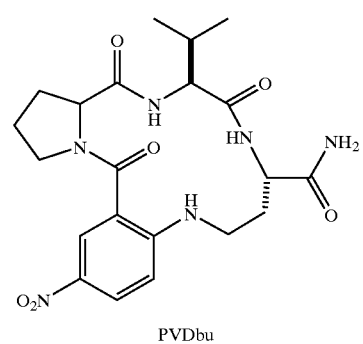

PVDbu

-continued
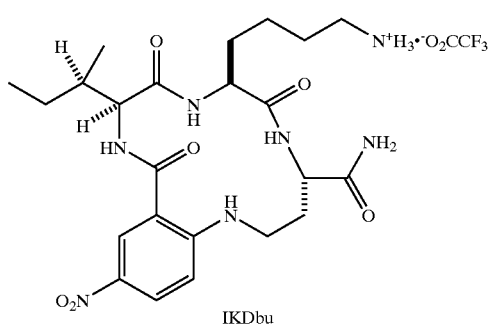
IKDbu
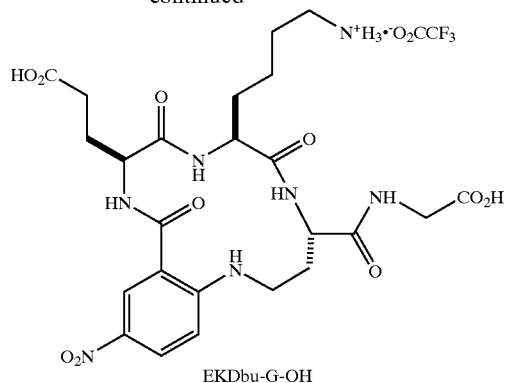
EKDbu-G-OH
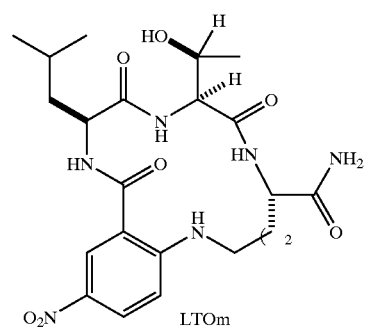
LTOm
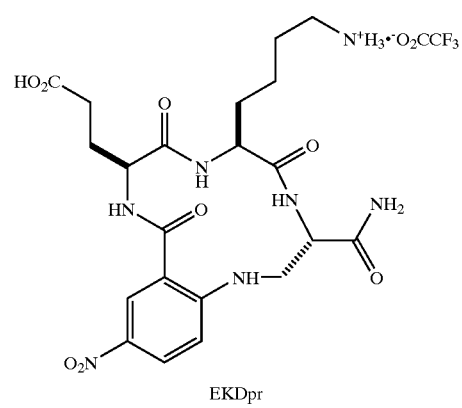
EKDpr
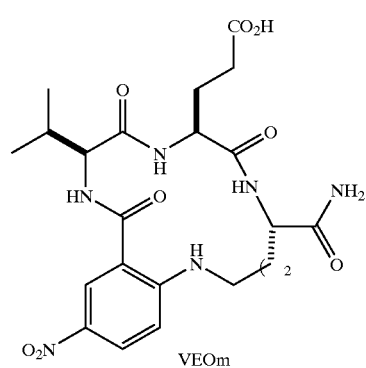
VEOm
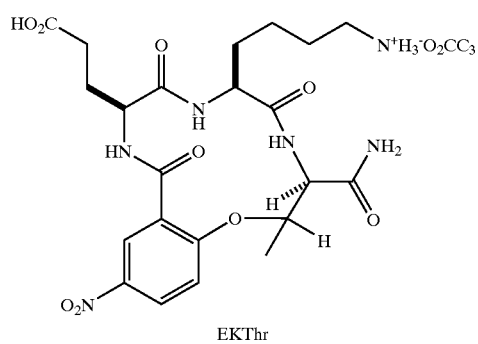
EKThr
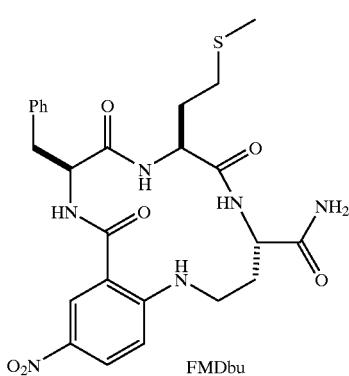
FMDbu
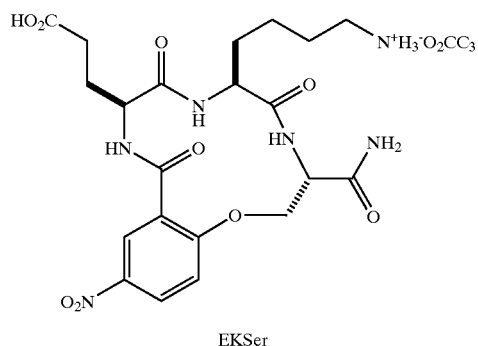
EKSer

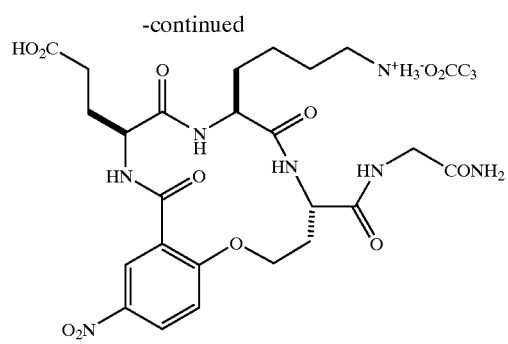
EKHse-G-NH₂
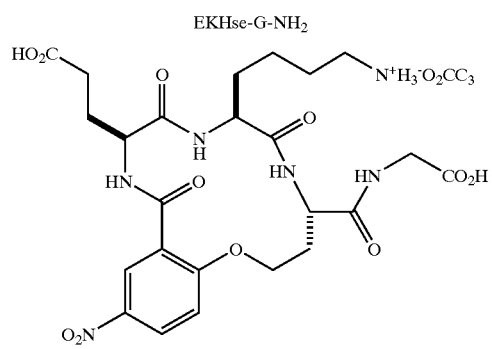
EKHse-G-OH
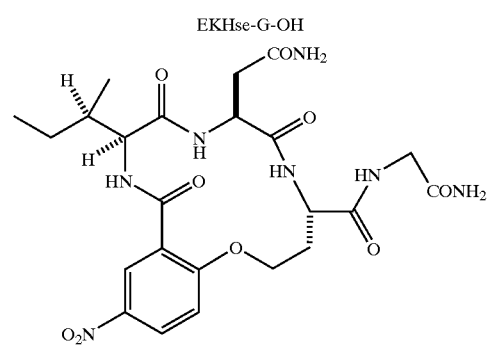
INHse-G-NH₂
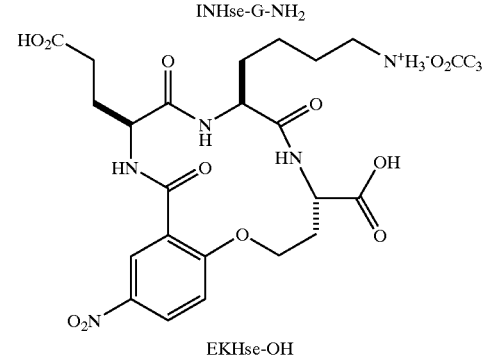
EKHse-OH
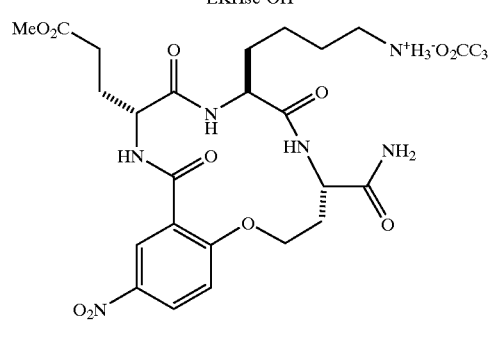
eKHse (methyl ester)
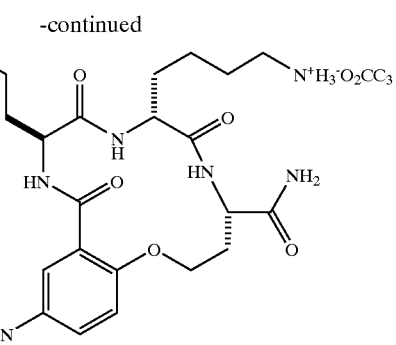
EkHse (methyl ester)
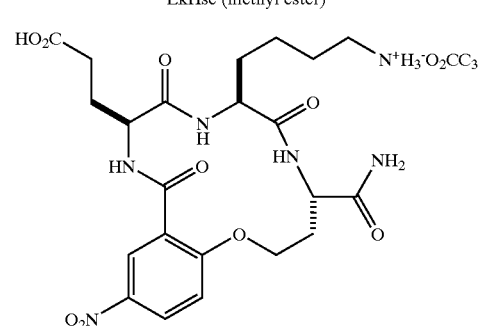
EKHse
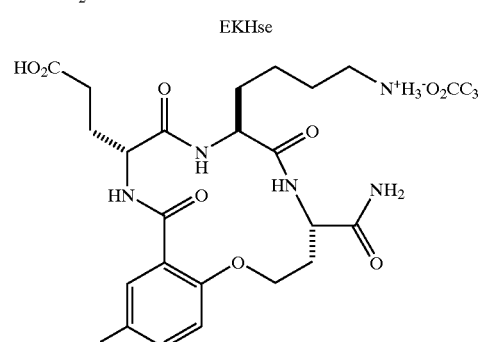
eKHse
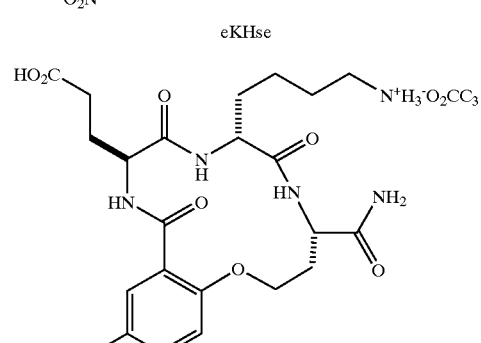
EkHse
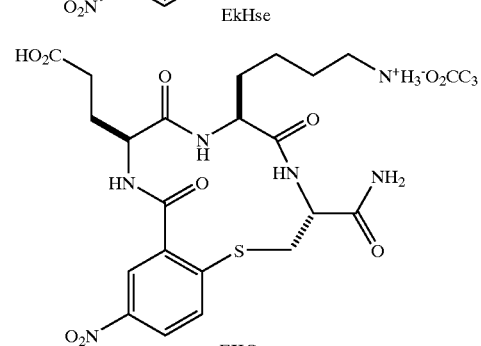
EKCys

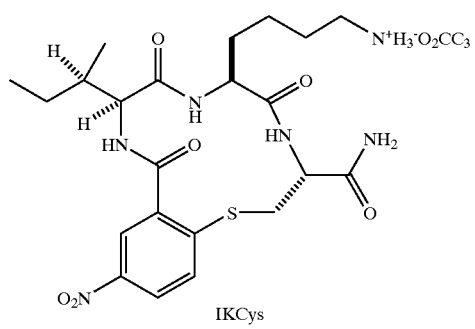
IKCys
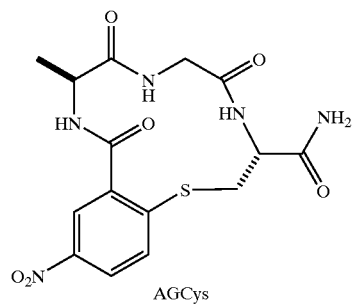
AGCys
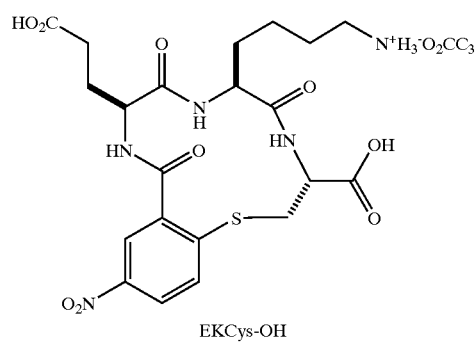
EKCys-OH
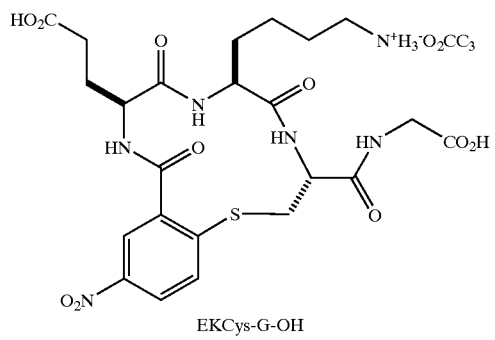
EKCys-G-OH
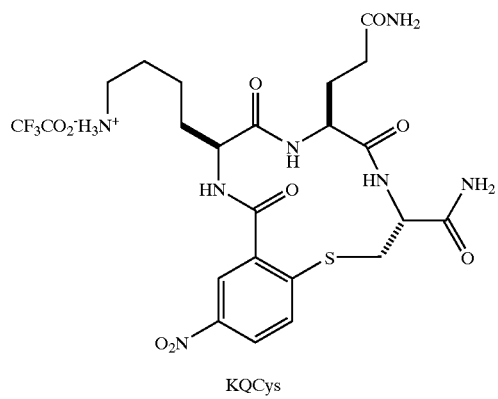
KQCys
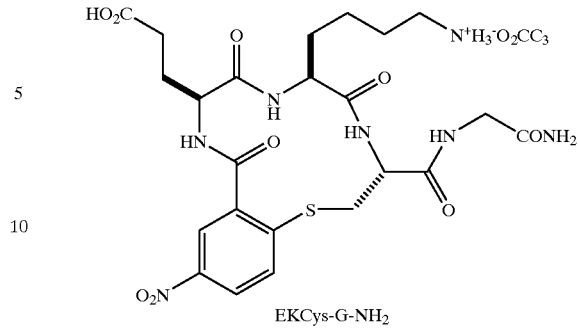
EKCys-G-NH₂
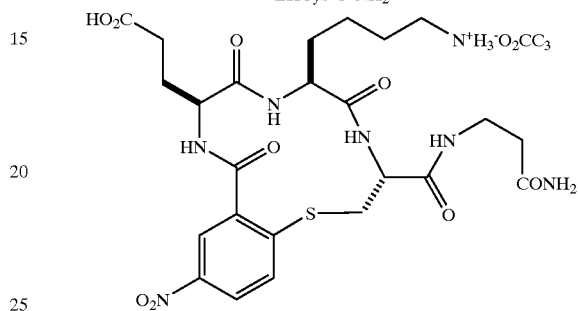
EKCys-βA-NH₂
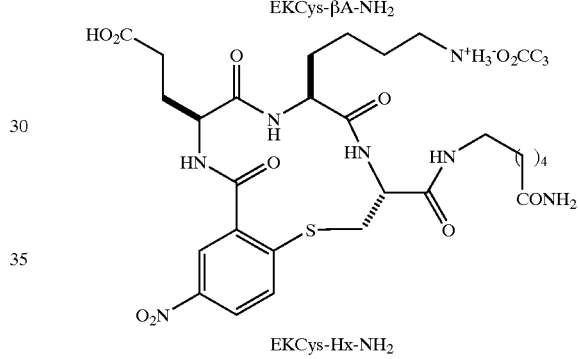
EKCys-Hx-NH₂
The cyclic compounds of the invention may be prepared according to the procedure described by Feng et al in J. Am. Chem. Soc. 1998, 120, 10768–1076. The general type of reaction is illustrated hereinafter
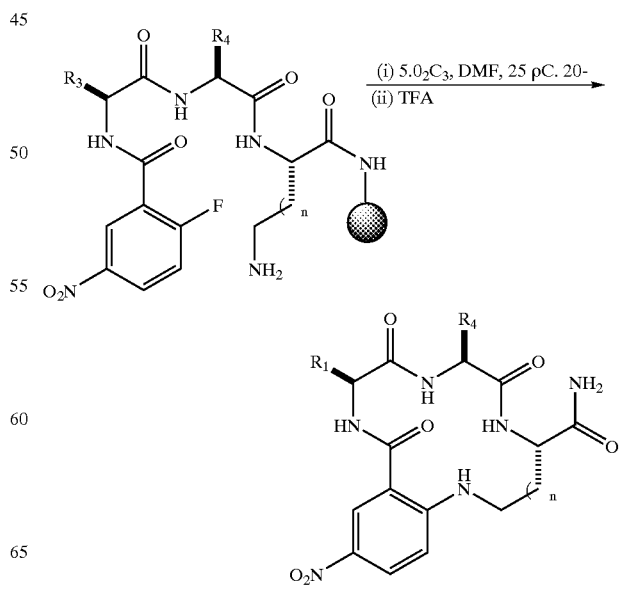

This is a solid-phase $S_NAr$ macrocyclization in which amino acids sequentially form peptide linkages of the macrocyclic ring. If necessary side chains on the peptido linkage may be protected, for example, as t.butyl esters or BOC-amides.

The substituent Y in formula (I) may be, for example, $NO_2$ which can be readily reduced to amino which may be employed to develop a biotin label; other labels that could be attached to substituent Y include radioactive elements such as iodine and technetium.

The invention is illustrated hereinafter by reference to the compound EKHse-G-OH referred to hereinafter for convenience as D3 and its biotin derivative referred to hereinafter as D3-Biotin and the compound EKCys referred to hereinafter for convenience as C59 and which is an analog of D3, the structures being indicated hereinafter

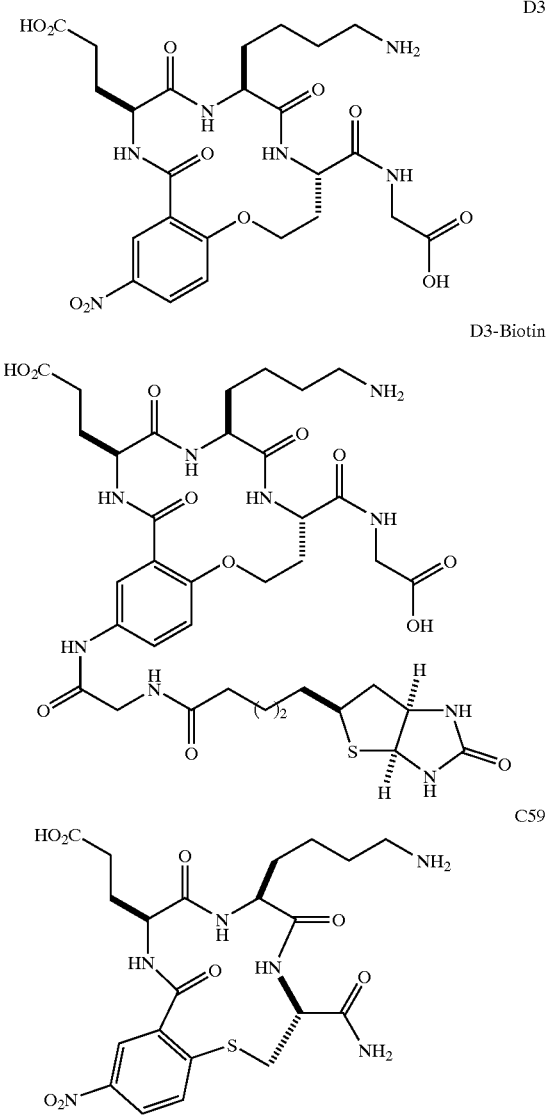

The neurotrophin receptor agonist or antagonist properties are most effectively utilized in the treatment of neurotrophin receptor mediated disorders when the cyclic compound is formulated into novel pharmaceutical compositions with a pharmaceutically acceptable carrier according to conventional pharmaceutical compounding techniques.

The novel compositions contain at least a therapeutic neurotrophin receptor agonist or antagonist amount of the active cyclic compound. Generally, the composition contains up to 0.1 to 100 mg/kg body weight of the patient of the cyclic compound. Concentrate compositions suitable for dilutions prior to use may contain 90 percent or more by weight. The compositions include compositions suitable for oral, rectal, topical, parenteral (including subcutaneous, intramuscular, and intravenous), pulmonary (nasal or buccal inhalation), nasal administration, or insufflation. The compositions may be prepacked by intimately mixing the cyclic compound with the components suitable for the medium desired.

When oral administration is to be employed, it may be with a liquid composition. For liquid preparations, the therapeutic agent is formulated with liquid carriers such as water, glycols, oils, alcohols, and the like, and for solid preparations such as capsules and tablets, solid carriers such as starches, sugars, kaolin, ethyl cellulose, calcium and sodium carbonate, calcium phosphate, kaolin, talc, lactose, generally with lubricant such as calcium stearate, together with binders, disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Composition in unit dosage form constitutes an aspect of the present invention.

The cyclic compound also may be formulated in therapeutic compositions for intravenous or intraperitoneal injection and may be presented in unit dosage form in ampoules or in multidose containers, if necessary with an added preservative. The compositions may also take such forms as suspensions, solutions or emulsions in oily or aqueous vehicles such as sodium chloride or dextrose in water, and may contain formulating agents such as suspending, stabilizing and/or dispersing agents. Buffering agents as well as additives such as saline or glucose may be added to make the solutions isotonic. The cyclic compound also may be solubilized in alcohol/propylene glycol or polyethyleneglycol for drip intravenous administration. Alternatively, the active ingredients may be in powder form for reconstituting with a suitable vehicle prior to administration.

The term "unit dosage form" herein refers to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the cyclic compounds.

For administration by inhalation, the cyclic compounds of the present invention are conveniently delivered in the form of an aerosol spray presentation from pressurized packs of nebulisers. The cyclic compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of the cyclic compound in suitable propellants, such as fluorocarbons or hydrocarbons.

Another method of administration is insufflation, particularly if the infection has spread to the ears and other body cavities.

If the application is to be topical, the cyclic compound may be formulated in conventional creams and ointments such as white petrolatum, anhydrous lanolin, cetyl alcohol, cold cream, glyceryl monostearate, rose water and the like.

BRIEF DESCRIPTION OF DRAWINGS

FIG. 2 demonstrates that D3 enhances cell surface TrkA.TrkA homodimers;

FIG. 3 illustrates NGF with highlighted turn regions believed to be critical for binding to the TrkA receptor (two zinc atoms are present in the dimer but are omitted for overall clarity.

DETAILED DESCRIPTION OF DRAWINGS

Figure 1:
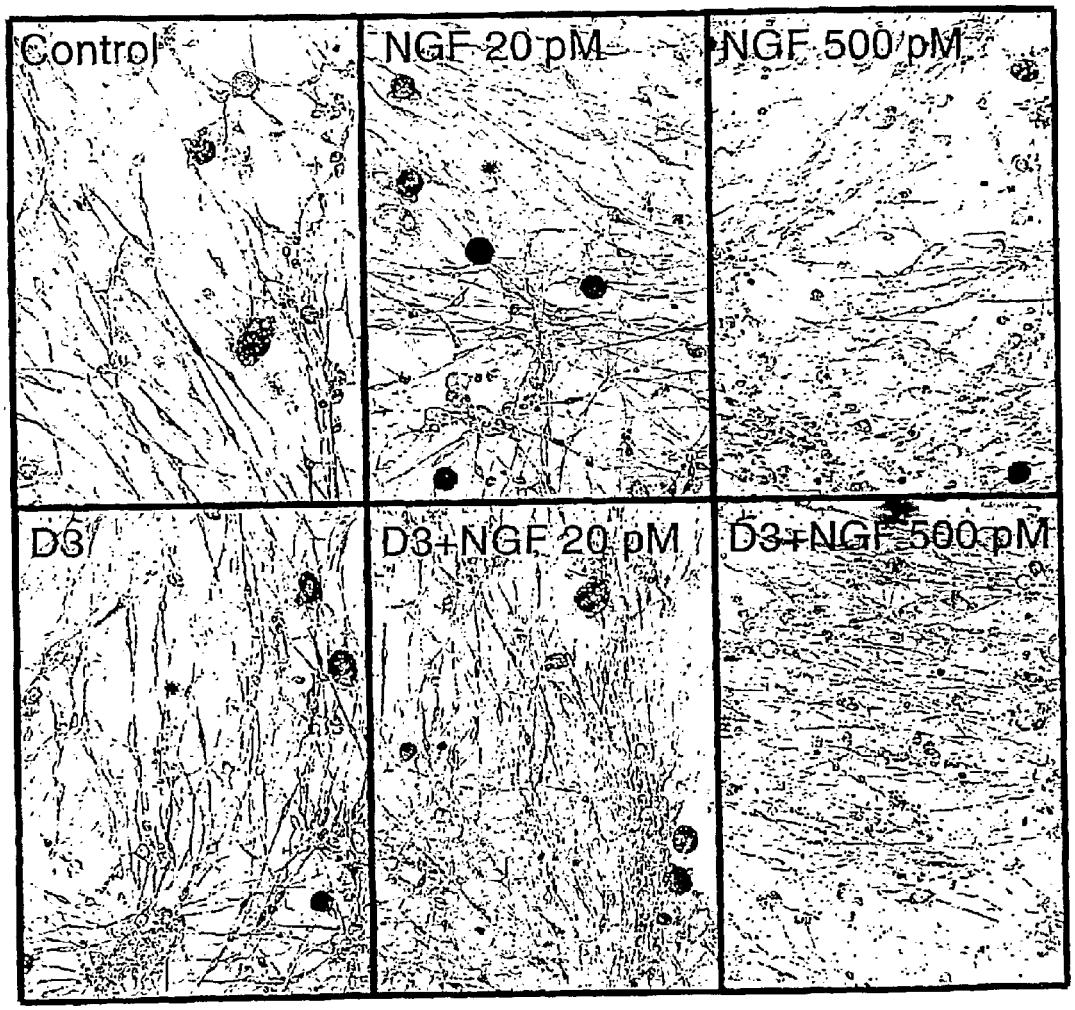
FIG. 1 demonstrates that D3 induces the partial differentiation of embryonic DRG cultures; when applied alone; and synergistic enhancement of the effect of suboptimal NGF concentrations.

In FIG. 1 primary neuronal DRG cultures were treated as indicated for 8 days, and cell differentiation was studied morphometrically. Magnification 60×. Pictures representative of 3 independent experiments.

Figure 4:
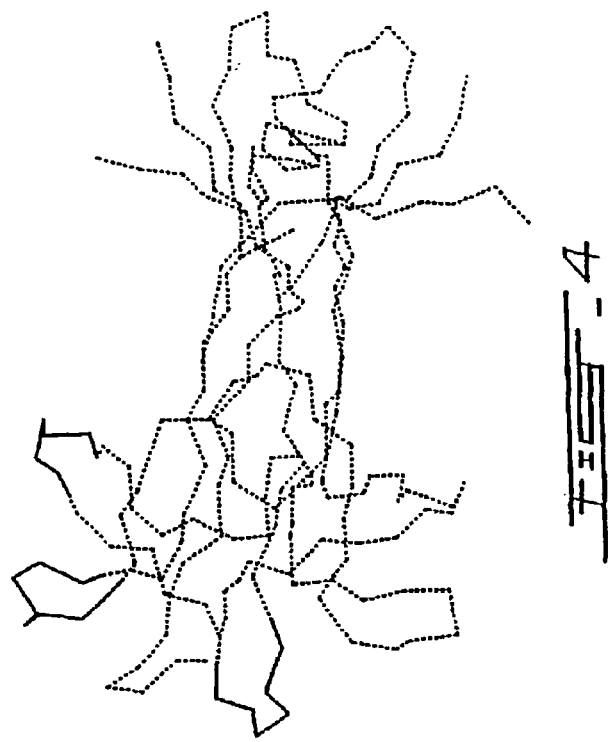
FIG. 4 illustrates the structure of NG-3/BDNF heterodimer with corresponding turn regions of NT-3 highlighted.
Figure 5:
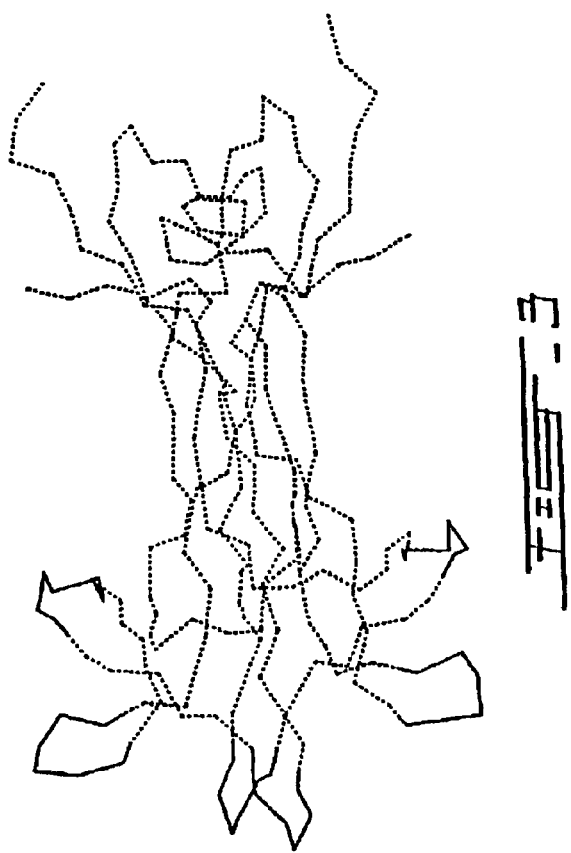

In FIG. 2, 4–3.6 cells were exposed to TrkA ligands as per Table 5 (lanes 1–4) or no ligand (lanes 5 and 6), and chemically cross-linked (lanes 1–5) or not cross-linked (lane 6). Cell lysates were western blotted with anti-TrkA 203 antisera. The intensity of the $M_r$ 300 kDa band was analyzed densitometrically from 4 experiments standardized to 1 nM NGF.

The compound D3 is a small, selective, and proteolytically stable agonist of the TrkA receptor. Furthermore, the docking site of D3 onto TrkA has been evaluated and demonstrates that a small peptidomimetic ligand can agonize a tyrosine kinase neurotrophin receptor that normally binds a relatively large protein ligand. The compounds of the invention thus offer an alternative therapeutic strategy with pharmacological agents that selectively target neuronal populations expressing specific neurotrophin receptors on the cell surface.

EXAMPLES

Materials and Methods
Preparation of D3 and D3-biotin

Compound D3 was prepared according to methods previously outlined for related compounds (Feng et al., 1998). FMOC-Gly, FMOC-Hse(Trt), FMOC-Lys(BOC), FMOC-Glu(OtBu), then 2-fluoro-5-nitrobenzoyl chloride were coupled (di-iso-propylcarbodiimide activation, 20% piperidine in DMF to remove FMOC groups) to TentaGel S PHB resin at 0.18 mmol/g loading. The supported peptide was treated six times with 1% TFA/4 5 HSiiPr$_3$ in CH$_2$Cl$_2$ for 5 min to remove only the Trt-protection. Cyclization was effected by treatment with 5.0 equivalents of K$_2$CO$_3$ in DMF for 40 h. After 90% TFA/5% H$_2$O/5% HSiiPr$_3$ cleavage, the final product was purified by reverse phase HPLC. D3 and its derivatives were soluble in water to 5 mg/ml (the highest concentration tested).

D3-biotin was prepared in the same way as D3, except that after the cyclization the nitro group was reduced by treatment with 10 equivalents of SnCl$_2$.2H$_2$O in DMF for 20 h. After reduction, FMOC-Gly, then biotin-N-hydroxysuccinimide was coupled to the newly formed arylamine. The product was then cleaved from the resin. The final product was purified by reverse phase HPLC.

Cell Lines:

B104 rat neuroblastomas express p75 receptors but do not express any of the Trks (TrkA– p75+). The 4–3.6 cells are B104 cells stably transfected with human trkA cDNA, and express equal levels of p75 and TrkA (TrkA+ p75+). For screening agents that activate or antagonize TrkC receptors, NIH3T3 fibroblasts were stably transfected with human TrkC cDNA. These cells respond to the ligand NT-3. For screening agents that activate or antagonize TrkA receptors, NIH3T3 fibroblasts were stably transfected with human TrkA cDNA. These cells respond to the ligand NGF. Wild type NIH3T3 fibroblasts were used as controls because they do not respond to any neurotrophin ligand.

Generation of Human TrkA-rat TrkB Chimeras in HEK293 Cells

The IgG-C2 domain of human TrkA was generated using unique restriction sites in the primers to allow exchange with the corresponding rat TrkB domain. The chimeric receptors were constructed by subcloning the human TrkA IgG-C2 domain into the corresponding restriction sites of the rat trkB cDNA reported in a previous work (Perez et al., 1995). Chimeric constructs were confirmed by sequencing, and were cloned into the pCDNA3 expression vector that contains a selection gene providing resistance to neomycin (G418, GIBCO). HEK293 cells were transfected using the lipofectamine plus method (GIBCO), selected with neomycin (0.5 mg/ml) and at least 3 independent subclones were obtained by limiting dilution techniques (293-TrkB/A-IgC2 chimera). Western blot analysis with polyclonal antibody 203 directed to the Trk intracellular domain and cell surface FACScan analysis with polyclonal antibody directed to the TrkA extracellular domain indicated that all stable subclones express comparable levels of chimeric receptors.

Dissociated Neuronal Dorsal Root Ganglia Cultures

Fetal rat DRG primary cultures were established from Sprague Dawley day 17 rat embryos. All ganglia were dissected and dissociated first enzymatically with trypsin and then mechanically. Dissociated cells were cultured ($10^5$ cells/well) in 96 well plates pre-coated with collagen, and grown for a total of 8 days in Neuro Basal Medium containing N2 supplement (GIBCO, Toronto), antibiotics, and L-glutamine. These DRG cultures are ~85% TrkA-expressing and are heavily dependent on TrkA signals for survival.

Septal Neuronal Cultures

Cell cultures were established from the septal area of 17-day-old rat embryos. In brief, tissue was incubated in PBS containing trypsin and DNase. Tissue pieces then were mechanically dissociated. After centrifugation, the pellet was suspended in Leibovitz's L-15 medium. Cells were plated onto 96-multiwell NUNC dishes ($10^5$ cells/well) coated with poly-D-lysine (5 µg/ml). Pure cultures of septal neurons were treated 1 day after plating. Drugs, prepared in medium, were added directly to the cells without changing the initial medium. The incubation continued for 8 days, at which time ChAT activity was evaluated.

D3•TrkA Binding Assays

Direct binding studies: were done as described (Saragovi et al., 1998) using 6 ng/well of recombinant baculovirus TrkA-extracellular domain protein (TrkA-ECD) or control bovine serum albumin (BSA, Fraction V, Boehringer Mannheim) immobilized onto 96-well microtest plates. Wells were blocked with binding buffer (BB: PBS with 1% BSA) for 1 hour. Then, 50 ng/well of biotinylated D3 were added as primary reagent in BB for 40 min in the absence or presence of excess non-biotinylated D3 as competitor. Wells were washed 5 times with BB, and horseradish peroxidase (HRP)-coupled avidin (Sigma) was added as secondary reagent for 30 min. Plates were washed in BB, and peroxidase activity was determined colorimetrically using 2,2-azinobis (3-ethylbenzthiazoline sulfonic acid) (ABTS, Sigma). The optical density (OD) was measured at 414 nm in a Microplate reader (Bio-Rad). Assays were repeated at least three times, n=4.

FACScan binding assays: 4–3.6 cells ($2 \times 10^5$) in FACScan binding buffer (PBS, 0.5% BSA, and 0.1% NaN3) were immunostained as described (Saragovi et al., 1998). Saturating anti-TrkA mAb 5C3, or anti-p75 mAb MC192, or control non-binding IgGs were added to cells for 1 hour at 4° C., in the presence or absence of D3 as competitor. Excess primary antibody was washed off, and cells were immunostained with fluorescinated goat-anti-mouse IgG secondary antibody. Cells were acquired on a FACScan and mean channel fluorescence of bell-shaped histograms were analyzed using the LYSIS II program.

Binding Competition: studies were as described for direct binding assays to TrkA-ECD, except that as primary reagent 50 ng anti-TrkA mAb 5C3/well were added in BB, in the presence or absence of D3 or controls as competitors as described (Saragovi et al., 1998). Wells were washed 5 times with BB, and HRP-coupled goat anti-mouse was added as secondary reagent for 30 min. Plates were washed in BB, and peroxidase activity were determined. Assays were repeated at least three times, n=4.

Cell Survival Assays

Primary DRG cultures: After a total of 8 days of culture with the indicated test or control ligands, cell survival were studied using the 3(4,5-Dimethylthiazolyl-2)-2,5-diphenyl tetrazolium bromide colorimetric (MTT) assay, and by microscopic observation.

Cell lines: 5,000 cells/well in protein-free media (PFHM-II, GIBCO, Toronto) containing 0.2% bovine serum albumin (BSA) (Crystalline fraction V, Sigma, St. Louis, Mo.) were seeded in 96 well plates (Falcon, Mississauga, Ontario). The cultures were untreated, or treated with the indicated test or control ligands. Cell viability was quantitated using the MTT assay after 56–72 hours of culture. Percent protection was standardized from optical density (OD) readings relative to optimal NGF (1 nM)=100%. The OD of untreated cells were subtracted. The higher optical density of untreated primary cultures is likely due to cellular heterogeneity and to endogenous production of limiting amounts of growth factors.

Measurement of ChAT Activity

At day 8 of culture, the medium was aspirated, and ice-cold lysis buffer (10 mM sodium phosphate, pH 7.4/0.1% TritonX-100—Trade-mark) was added. ChAT activity assays were performed directly in the wells using Fonnum's method (Fonnum, 1975).

Detection of Putative TrkA•TrkA Homodimers

Live 4–3.6 cells suspended in PBS were treated with the indicated ligand(s) for 40 min at 4° C. to allow binding. Cells were then washed in PBS, cross-linked with the membrane impermeable cross-linker disuccinimidyl suberate (DSS, Pierce; 1 mM DSS, 15 minutes at 15° C.). Unreacted DSS was quenched with 5 mM ammonium acetate. Then cells were either lysed directly in SDS sample buffer (whole cell lysate), or lysed in non-ionic detergent NP-40 and immunoprecipitated with anti-Trk or anti-p75 antibodies as described (LeSauteur et al., 1996). Similar results were obtained with either method. For western blot analysis, equal amounts of protein or cell equivalents for each sample were resolved in a 5–10% SDS-PAGE gradient, transferred to nitrocellulose membranes (Xymotech Biosystems, Montréal, Qc), and blotted with anti-Trk polyclonal antibody 203 that recognizes the intracellular domain of Trk. Blots were visualized using the enhanced chemiluminescence (ECL) system (New England Nuclear, Boston, Mass.).

RESULTS

Synthesis of Focussed β-Turn Peptidomimetic Libraries

A solid phase synthesis was developed to yield a macrocyclic ring with the i+1 and i+2 residues of a β-turn in the appropriate conformation. Approximately 60 compounds of this type were prepared (Feng et al., 1998), with amino acid side chains incorporated to correspond to β-turns of NGF and mAb 5C3 implicated in docking to TrkA (LeSauteur et al., 1996; LeSauteur et al., 1995). TrkA binding is mediated by discrete β-turn regions of these ligands. Cyclic peptide β-turn analogs of NGF and of mAb 5C3 were active only in the appropriate conformation (Beglova et al., 1998).

C59 found to be inactive was used as a negative control. A biotinylated form of D3, D3-biotin, was synthesized to carry out direct binding studies to TrkA. All ligands were highly soluble in physiological buffers and did not require organic solvents.

D3 is a Selective Ligand of TrkA

FACScan analysis featuring the secondary fluorescent agent avidin-FITC was used to detect binding of D3-biotin to the cell surface (Table 1). The 4–3.6 cells (p75+TrkA+) had fluorescence approximately 4 times greater for D3-biotin than for a background control peptide-biotin. Moreover, a 10-fold molar excess of D3 abolished binding of D3-biotin. In contrast, no specific binding was measured for B104 cells (p75+TrkA−). Since 4–3.6 cells are B104 cells stably transfected with TrkA cDNA and these cell lines are otherwise identical, the data indicate that D3-biotin and D3 bind cell surface TrkA.

Similar binding data for D3-biotin was obtained by ELISA using pure soluble TrkA extracellular domain (TrkA-ECD) produced in baculovirus (see Table 3). These data further indicate that D3 binds to the extracellular domain of TrkA, and that membrane lipids are not required.

D3 Binds within an Agonistic Site of TrkA

Previously, mAb 5C3 was shown to act as a full TrkA agonist. MAb 5C3 binds with $K_d$ 2 nM (LeSauteur et al., 1996) at an epitope within the IgC2 domain of TrkA near the NGF binding site. This site is postulated to define a receptor "hot spot". D3 and mAb 5C3 were tested to determine if they bind to overlapping receptor sites.

Two related assays tested the ability of D3 to compete for the binding of the full TrkA agonist mAb 5C3. In the first test, a FACScan-based assay using intact cells, D3-induced a dose-dependent competitive decrease of mAb 5C3•TrkA interactions (Table 2, rows 2–5). On average, D3 exhibited an $IC_{50}$ of 4 µM. From experimental conditions a $K_d$ ~2 µM for D3•TrkA interactions is estimated. Blocking of 5C3•TrkA interactions by D3 is selective because the binding of mAb MC192 directed to the p75 NGF receptor subunit was not blocked (Table 2, rows 7 vs 8). Furthermore, inactive control C59 peptidomimetic did not inhibit the binding of either mAb 5C3 (Table 2, row 6) or mAb MC192.

The second test used purified recombinant TrkA extracellular domain (TrkA-ECD) immobilized onto ELISA plates to assay competitive blocking of 5C3•TrkA-ECD by D3. D3 exhibited a dose-dependent inhibition of 5C3•TrkA-ECD interactions, but control inactive C59 peptidomimetic had no effect (Table 3). Since a $K_d$ ~2 nM was measured for 5C3•TrkA interactions, from the experimental $IC_{50}$ a $K_d$ ~2

μM was calculated for D3•TrkA-ECD interactions. This calculation is consistent with the data shown in Table 2. Interestingly, similar ELISA and RIA binding assays revealed that D3 did not substantially block NGF•TrkA-ECD interactions.

D3 Affords Trophic Activity Selectively via TrkA, and is Proteolytically Stable

Since D3 binds at or near an agonistic site of TrkA, trophic effects were probed in cell survival assays using the quantitative MTT method. Several doses of D3 were tested. However, for clarity only near optimal concentrations are shown, which approximate the estimated $K_d$.

Dissociated primary neuronal cultures from fetal dorsal root ganglia (DRG) are dependent on TrkA agonists for survival. Exogenous NGF showed a dose-dependent trophic effect (Table 4, rows 2–4). D3 alone had a significant protective effect on DRG cultures (Table 4, row 5) but control C59 did not (Table 4, row 6). Primary cultures are heterogeneous and low levels of neurotrophins are made endogenously, which explains a relatively high optical density for untreated cultures (Table 4, row 1).

Since D3 does not block NGF binding, potential synergy between NGF and D3 was assessed. D3 combined with different concentrations of exogenous NGF demonstrated an additive or potentiating effect on DRG survival (Table 4, rows 7–9).

Similar results were obtained with other neuronal cell lines, wherein D3 potentiated the effect of low NGF concentrations (Table 5). Optimal protection of 4–3.6 cells (p75+TrkA+) and HEK293-TrkB/A-IgC2 chimeras corresponded to treatment with 1 nM NGF (Table 5, row 2) whereas 10 pM NGF gave significantly less protection (Table 5, row 3). D3 alone afforded low but significant protection (Table 5, row 4), and protection was enhanced with a combination of 10 pM NGF+10 μM D3 (Table 5, row 6). The negative control C59 compound had no effect alone or in enhancing 10 pM NGF (Table 5, rows 5 and 7).

In other controls, neither D3 nor NGF protected B104 cells, wild type HEK293 cells, or TrkB-expressing HEK293 cells from apoptosis. Hence the trophic activity of NGF and D3 require TrkA expression, or at least the IgG-C2 domain of TrkA. Additionally, D3 did not enhance the trophic effect of EGF suggesting that it may be NGF selective. Lastly, D3 enhanced NGF protection of NIH3T3 cells stably transfected with TrkA cDNA but did not enhance NT-3 protection of NIH3T3 cells stably transfected with trkC cDNA. These data indicate that D3 selectively accentuates the trophic effect of NGF, and that expression of the p75 low affinity NGF receptor is not required.

The proteolytic stability of D3 versus trypsin and papain was assessed. D3 was first exposed to enzymatic treatment as described previously (Saragovi et al., 1992), followed by gauging its biological activity on 4–3.6 cells. Compound D3 remained fully active in trophic assays even after 1 hour of exposure to trypsin or pepsin, whereas NGF lost all activity within minutes under the same conditions.

D3 Induces Differentiation of Primary Cultures of Fetal DRG and Fetal Septal Neurons The effect of D3 on TrkA-mediated cellular differentiation was assessed using two independent assays: morphometric analysis of DRG dissociated neurons and induction of ChAT activity in septal neuronal cultures. In the first of these assays, data indicate that DRG neuronal cultures undergo neurite outgrowth in response to D3, and that D3 potentiates the effect of NGF (FIG. 1). In the second assay, ChAT activity was found to increase in response to NGF (Table 6, rows 1 and 2) and to D3 alone (Table 6, rows 3–5), whereas C59 control had no effect (Table 6, row 6). Increases in ChAT activity in response to 2 μM D3 alone were comparable to 10 pM exogenous NGF. Moreover, combinations of 2 μM D3+10 pM NGF markedly increased ChAT activity, and were more effective than 400 pM NGF (Table 6, rows 8–10).

D3 Enhances or Stabilizes Putative TrkA•TrkA Homodimers

Based on the data above, it was expected that D3 would induce or stabilize TrkA•TrkA interactions. This hypothesis was studied biochemically in 4–3.6 cells exposed to ligands, followed by cell surface chemical cross-linking (FIG. 2).

The expected doublet consistent with previously reported TrkA monomers of p110 and p140 were seen in all samples (FIG. 2, thick arrow). Bands of ~300 kDa, consistent with the molecular weight of TrkA•TrkA homodimers (FIG. 2, thin arrow), were seen in samples from cells treated with TrkA ligands 1 nM NGF, 10 pM NGF, or 10 pM NGF+10 μM D3, and was also detected (albeit very more weakly) in cells treated with 10 μM D3 alone. The intensity of the band $M_r$ 300 kDa, presumed to be TrkA dimers, was analyzed densitometrically from 4 independent experiments standardized to 1 nM NGF (100%). There was a consistent increase in dimers after treatment with D3 alone (21±4%) or 10 pM NGF alone (52±6%), which was higher after treatment with 10 pM NGF+10 μM D3 (77±7%). Control cells cross-linked in the absence of ligand or cells exposed to ligand but not-cross-linked did not have putative dimers.

TrkA homodimers are stable to SDS denaturation because of covalent cross-linking. Given that the efficiency of chemical cross-linking is ~1–4% of the total TrkA pool further biochemical characterization of the complexes was precluded, other than the fact that they contain TrkA. The complexes may contain cross-linked NGF. However, it is unlikely that the bands comprise p75 because immunoprecipitations with anti-p75 antibodies did not reveal any material in the $M_r$ of TrkA homodimers. Furthermore, material of $M_r$ 215 kDa that would comprise p75-TrkA heterodimers was not seen consistently.

Biological Activity of Examples of Preferred Embodiments

Examples of some preferred embodiments that mimic NGF-like neurotrophic activity (Table 7) are agents termed D3, D53b–d, D21, P23, and P58. These agents, tested at 10 μM, afford significant survival to cells expressing TrkA, but not to cells that do not express neurotrophin receptors. Additionally, these agents synergize with suboptimal concentrations of NGF (10 pM). NGF at 10 pM affords 32±6% survival compared to 1 nM NGF which in TrkA cells is standardized to 100% survival. NGF at 10 pM plus the indicated embodiments significantly enhances cell survival.

Examples of some preferred embodiments that mimic NT-3-like neurotrophic activity (Table 8) are agents termed P27 and P23. These agents, tested at 10 μM, afford significant survival to cells expressing TrkC, but not to cells that do not express neurotrophin receptors. Additionally, these agents synergize with suboptimal concentrations of NT-3 (10 pM). NT-3 at 10 pM affords 29±1% survival compared to 1 nM NT-3 which in TrkC cells is standardized to 100% survival. NT-3 at 10 pM plus the indicated embodiments significantly enhances cell survival. Note that P23 enhances survival of cells expressing TrkA and TrkC, hence it behaves as NT-3 which is a ligand of both receptors.

Examples of some preferred embodiments that antagonize NGF neurotrophic activity (Table 9) are agents termed P42 and P43. While these embodiments alone do not affect cell survival (Table 9, rows 4 and 5), they do reduce the survival afforded by NGF (Table 9, rows 6–9). NGF at 1 nM (Table 9, row 2) affords 100% survival and this effect is reduced by P42 and by P43 respectively to 68% and 55% survival. Hence these embodiments are antagonistic to NGF neurotrophic activity.

Discussion

A proteolytically stable β-turn peptidomimetic small molecule agonist of the TrkA neurotrophin receptor. We showed that D3 binds TrkA, competes the binding of the TrkA agonist mAb 5C3, selectively potentiates trophic protection of TrkA-expressing cell lines and neuronal primary cultures, and induces the differentiation of primary neuronal cultures. These results indicate that a small β-turn peptidomimetic can activate a tyrosine kinase neurotrophin receptor that normally binds a relatively large protein ligand.

Recent advances in ligand mimicry have resulted from screening large phage or peptide libraries, natural products, or chemical libraries. However, most of the ligands described are antagonists, or otherwise require the dimerization of relatively large peptides, have a 2-fold axis of symmetry that resemble a dimer, or are poorly soluble in physiological buffers. In contrast, D3 is a small, non-symmetrical, proteolytically stable, highly water soluble peptidomimetic that binds the extracellular domain of TrkA.

Binding and ligand competition studies demonstrate selective interaction of D3 with the extracellular domain of TrkA, rather than the catalytic domain. Hence, the water solubility and extracellular targeting of D3 mean that toxic organic solvents are not required to permeate the cell membrane.

What is the Role of pM Concentrations of NGF?

Given the low concentrations used in synergy with D3, it is unlikely that the effect of NGF was mediated by docking with the low affinity receptor p75. It is postulated that NGF acts by increasing TrkA•TrkA interactions whereas D3 stabilizes the homodimers or reduces the rate of separation of receptor homodimers by inducing conformational changes.

In the present invention, the biological data shown are with low μM concentrations of D3, which are optimal. As expected from the affinity estimated for TrkA•D3 interactions, lower D3 concentrations afford lower efficacy. It is noteworthy that while NGF•TrkA affinity is ~$10^{-11}$ M, optimal activity requires 2 nM NGF concentrations. Hence, D3 is optimal at concentrations that approximate its $K_d$ while NGF is optimal at concentrations ~100 fold over its $K_d$. This difference is interpreted to mean that D3 is more stable in solution, and this notion is supported by D3 resistance to proteolysis.

Ligand Binding Sites

D3 competitively blocks the binding of mAb 5C3 but it does not block NGF. Moreover, the optimal agonistic activity of mAb 5C3 was inhibited by D3 in a dose-dependent manner, while the agonistic effect of NGF was enhanced. It is unlikely that D3 does not block NGF because of affinity differences, because NGF•TrkA-ECD and 5C3•TrkA-ECD interactions are both in the nM range.

Two factors could account for this result. First, both mAb 5C3 and D3 dock onto a single and continuous epitope within the IgG-C2 domain of TrkA, whereas NGF binds a discontinuous epitope within the IgG-C1 and IgG-C2 domains of TrkA (Perez et al., 1995), and other domains. This would facilitate mAb 5C3 blocking by D3 whereas NGF could bind via its second docking site. Second, mAb 5C3 and NGF bind TrkA at sites partially overlapping but not identical (LeSauteur et al., 1996). Hence the data suggest that D3 binds TrkA at an epitope overlapping the agonistic mAb 5C3 "hot spot" of the IgG-C2 domain of TrkA, near the NGF docking site. These observations may account for D3 synergizing with NGF and blocking mAb 5C3. The docking site is called "hot spot" because it defines a functional site wherein ligands that bind the site can trigger a function. That function may be (partial) agonistic or (partial) antagonistic.

The fact that D3 is bioactive and was selected from a relatively small pool of β-turn based compounds has broad implications for many research initiatives involving protein-protein interactions. Particularly these notions can be applied to all members of the neurotrophin family of ligands and their receptors because they all function in a manner comparable to TrkA.NGF.

The present invention provides a small molecule peptidomimetic that binds and activates TrkA. In the present invention it is found that a hybrid of a peptide and a small organic molecule designed to hold key amino acid residues in a turn conformation within a small framework offers a means to transform a peptide lead into an active organic small molecule. Hence, D3 represents the validation of the peptidomimetic concept for the Trk family of tyrosine kinase receptors. This small molecule peptidomimetic ligand of TrkA that has neurotrophic activity may be used to address neurodegenerative disorders, pain, neoplasias, and other pathologies (reviewed in (Saragovi and Burgess, 1999)) where Trk receptors play a role.

TABLE 1

D3 and D3-biotin bind TrkA.
Binding of biotin-D3 to B104 cells (p75+ TrkA-) or 4–3.6 cells (p75+ TrkA+) was quantitated by FACScan analysis. Ligands are control-biotin (an inactive biotinylated peptide) (row 2), D3-biotin (row 3), or D3-biotin with a 10-fold molar excess of D3 (row 4). All ligands were followed with avidin-FITC as a flourescent label. Data shown are mean channel flourescence (MCF) of bell-shaped histograms, 5,000 events acquired. MCF data ± sem are averaged from 3 independent experiments.

|  | MCF | |
| --- | --- | --- |
| Ligand | B104 | 4–3.6 |
| untreated | 10 ± 3 | 13 ± 2 |
| control-biotin 20 μM | 11 ± 1 | 10 ± 3 |
| D3-biotin 20 μM | 10 ± 4 | 53 ± 4 |
| D3-bio 20 μM + D3 200 μM | 11 ± 2 | 17 ± 7 |

TABLE 2

D3 specifically blocks mAb 5C3 binding to cell surface TrkA.
4–3.6 cells were analyzed by FACScan for binding of anti-TrkA mAb 5C3 or anti-p75 mAb MC192. Cells exposed to control primary mouse IgG with or without 40 μM D3 afford identical background staining. For each condition 5,000 cells were acquired. Percentage maximal bindings were calculated from the MCF of bell-shaped histograms, using the formula (TEST$_{MCF}$-background$_{MCF}$)*100/ MAXIMAL$_{MCF}$-background$_{MCF}$). MCF ± sem are averaged from 3 independent experiments.

|  | MAb (1 nM) | Competitor | Dose (μM) | % Maximal binding |
| --- | --- | --- | --- | --- |
| 1 | 5C3 | none | 0 | 100 ± 0 |
| 2 | 5C3 | D3 | 0.20 | 95 ± 4 |
| 3 | 5C3 | D3 | 1 | 80 ± 3 |
| 4 | 5C3 | D3 | 5 | 53 ± 5 |
| 5 | 5C3 | D3 | 40 | 33 ± 4 |
| 6 | 5C3 | C59 control | 40 | 97 ± 6 |
| 7 | MC192 | none | 0 | 100 ± 0 |
| 8 | MC192 | D3 | 40 | 101 ± 2 |

TABLE 3

D3 inhibits 5C3 · TrkA interactions in vitro.
The binding of mAb 5C3 (at constant 2 nM) to purified TrkA-ECD immobilized onto ELISA plates was measured in the absence or presence of competitors. Background (<2%) was the optical density of wells with all reactants except immobilized TrkA-ECD. Data are averaged from 3 experiments, each experiment n = 4.

|   | Competitor added | Concentration ($\mu$M) | % Binding ± sem |
|---|---|---|---|
| 1 | — | — | 100 ± 3 |
| 2 | D3 | 0.05 | 100 ± 14 |
| 3 | D3 | 0.2 | 89 ± 8 |
| 4 | D3 | 1 | 64 ± 10 |
| 5 | D3 | 5 | 43 ± 12 |
| 6 | D3 | 20 | 38 ± 7 |
| 7 | D3 | 40 | 31 ± 4 |
| 8 | C59 | 40 | 96 ± 9 |

TABLE 4

D3 protects TrkA-expressing primary neurons from apoptosis. and potentiates NGF.
NGF-dependent primary neuronal cultures from embryonic rat DRGs were treated with the indicated ligands for a total of 8 days. Cell survival was measured by MTT assays. Protection was calculated relative to optimal NGF (1 nM, 100% protection) with subtraction of the O.D. of untreated cells. Shown is the O.D. from one experiment, mean ± sem, n = 4. % protection was averaged from 3 experiments.

|   | Treatment | Optical Density | % Protection |
|---|---|---|---|
| 1 | untreated | 256 ± 15 | 0 ± 2 |
| 2 | NGF 1 nM | 823 ± 28 | 100 ± 4 |
| 3 | NGF 20 pM | 316 ± 11 | 9 ± 1 |
| 4 | NGF 500 pM | 535 ± 19 | 68 ± 3 |
| 5 | D3 10 $\mu$M | 405 ± 22 | 38 ± 2 |
| 6 | Control C59 10 $\mu$M | 271 ± 8 | 0 ± 1 |
| 7 | D3 10 $\mu$M + NGF 20 pM | 471 ± 28 | 48 ± 3 |
| 8 | D3 10 $\mu$M + NGF 500 pM | 603 ± 26 | 84 ± 3 |
| 9 | D3 10 $\mu$M + NGF 1 nM | 977 ± 38 | 120 ± 7 |

TABLE 5

D3 potentiates NGF in protecting TrkA-expressing cell lines from apoptosis by binding to the IgC2 domain of the receptor.
4–3.6 cells or HEK 293 cells expressing TrkB/TrkA IgG-C2 chimeric receptor were treated with the indicated ligands for a total of 72 hours. Survival was measured by MTT assays. % Protection was calculated as in Table 4. Shown is the O.D. from one experiment, mean ± sem, n = 4. Percent protection was averaged from 6 (4–3.6 cells) or 3 (293-IgG-C2 chimera) independent experiments.

|   |   | 4–3.6 cells | | HEK 293-TrkB/ TrkA chimera | |
|---|---|---|---|---|---|
|   | Treatment | Optical Density | % Protection | Optical Density | % Protection |
| 1 | untreated | 64 ± 7 | 0 ± 2 | 32 ± 5 | 0 ± 4 |
| 2 | 1 nM NGF | 412 ± 24 | 100 ± 6 | 350 ± 12 | 100 ± 4 |
| 3 | 10 pM NGF | 205 ± 19 | 40 ± 5 | 88 ± 8 | 18 ± 5 |
| 4 | 10 $\mu$M D3 | 95 ± 9 | 8 ± 2 | 69 ± 7 | 9 ± 3 |
| 5 | 10 $\mu$M C59 | 76 ± 4 | 2 ± 1 | 30 ± 7 | −1 ± 2 |
| 6 | 10 $\mu$M D3 + 10 pM NGF | 255 ± 14 | 55 ± 3 | 165 ± 11 | 42 ± 5 |
| 7 | 10 $\mu$M C59 + 10 pM NGF | 209 ± 17 | 41 ± 4 | 90 ± 9 | 21 ± 6 |

TABLE 6

D3 induces ChAT synthesis.
Septal neuronal cultures were treated as indicated for a total of 8 days. ChAT activity (pmol Ach/min/well ± sem) was measured at day 8. Average ± sem. Data averaged from 3 independent experiments, each experiment n = 4.

|   | Treatment | ChAT Activity | Fold Increase |
|---|---|---|---|
| 1 | 10 pM NGF | 0.42 ± 0.07 | 1.4 |
| 2 | 400 pM NGF | 0.72 ± 0.10 | 2.41 |
| 3 | 0.2 $\mu$M D3 | 0.37 ± 0.05 | 1.23 |
| 4 | 2 $\mu$M D3 | 0.44 ± 0.02 | 1.47 |
| 5 | 20 $\mu$M D3 | 0.48 ± 0.06 | 1.56 |
| 6 | 20 $\mu$M C59 control | 0.30 ± 0.04 | 1 |
| 7 | untreated | 0.31 ± 0.07 | 1 |
| 8 | 0.2 $\mu$M D3 + 10 pM NGF | 0.60 ± 0.04 | 2.00 |
| 9 | 2 $\mu$M D3 + 10 pM NGF | 0.76 ± 0.03 | 2.53 |
| 10 | 20 $\mu$M D3 + 10 pM NGF | 0.79 ± 0.04 | 2.63 |

TABLE 7

TrkA agonistic activity of examples of preferred embodiments
NIH3T3 fibroblasts transfected with and expressing TrkA or TrkC receptors, or untransfected wild type controls (NIH wt), were treated with the indicated ligands for a total of 72 hours. TrkA-expressing cells respond optimally to NGF. TrkC-expressing cells respond optimally to NT-3. Tests were done with agents alone or in the presence of suboptimal concentrations of NGF (10 pM). Survival was measured by MTT assays. % Protection was calculated as in Table 4. Shown is the O.D. from one experiment, mean ± sem, n = 4. Each experiment was repeated 3 times or more.

|   | Treatment | NIH-TrkA % Protection | NIH-TrkC % Protection | NIH wt % Protection |
|---|---|---|---|---|
| 1 | untreated | 0 ± 4 | 0 ± 2 | 0 ± 5 |
| 2 | 1 nM NGF | 100 ± 2 | 5 ± 6 | 5 ± 12 |
| 3 | 10 pM NGF | 32 ± 6 | 2 ± 4 | 5 ± 7 |
| 6 | 10 $\mu$M D3 | 8 ± 4 | 3 ± 3 | −3 ± 5 |
| 7 | 10 $\mu$M D3 + 10 pM NGF | 51 ± 5 | 6 ± 2 | 0 ± 3 |
| 10 | 10 $\mu$M D53b–d | 11 ± 4 | 4 ± 2 | 3 ± 5 |
| 11 | 10 $\mu$M D53b–d + 10 pM NGF | 45 ± 4 | 3 ± 1 | −4 ± 6 |
| 12 | 10 $\mu$M D21 | 16 ± 3 | 6 ± 4 | 3 ± 2 |
| 13 | 10 $\mu$M D21 + 10 pM NGF | 60 ± 5 | 5 ± 1 | 3 ± 3 |
| 14 | 10 $\mu$M P23 | 15 ± 2 | 8 ± 2 | 0 ± 3 |
| 15 | 10 $\mu$M P23 + 10 pM NGF | 52 ± 3 | 11 ± 5 | 1 ± 3 |
| 16 | 10 $\mu$M P58 | 21 ± 7 | 6 ± 5 | −1 ± 3 |
| 17 | 10 $\mu$M P58 + 10 pM NGF | 43 ± 6 | 5 ± 3 | 4 ± 2 |

TABLE 8

TrkC agonistic activity of examples of preferred embodiments
NIH3T3 fibroblasts transfected with and expressing TrkA or TrkC receptors, or untransfected wild type controls (NIH wt), were treated with the indicated ligands for a total of 72 hours. TrkA-expressing cells respond optimally to NGF and to a lesser degree to NT-3. TrkC-expressing cells respond optimally to NT-3. Tests were done with agents alone or in the presence of suboptimal concentrations of NT-3 (10 pM). Survival was measured by MTT assays. % Protection was calculated as in Table 4. Shown is the O.D. from one experiment, mean ± sem, n = 4. Each experiment was repeated 3 times or more.

|   | Treatment | NIH-TrkA % Protection | NIH-TrkC % Protection | NIH wt % Protection |
|---|---|---|---|---|
| 1 | untreated | 0 ± 4 | 0 ± 2 | 0 ± 5 |
| 2 | 1 nM NT-3 | 17 ± 3 | 100 ± 2 | −2 ± 5 |
| 3 | 10 pM NT-3 | 3 ± 2 | 29 ± 1 | 1 ± 4 |

TABLE 8-continued

TrkC agonistic activity of examples of preferred embodiments
NIH3T3 fibroblasts transfected with and expressing TrkA or TrkC
receptors, or untransfected wild type controls (NIH wt), were treated
with the indicated ligands for a total of 72 hours. TrkA-expressing
cells respond optimally to NGF and to a lesser degree to NT-3.
TrkC-expressing cells respond optimally to NT-3. Tests were done with
agents alone or in the presence of suboptimal concentrations of NT-3
(10 pM). Survival was measured by MTT assays. % Protection was
calculated as in Table 4. Shown is the O.D. from one experiment,
mean ± sem, n = 4. Each experiment was repeated 3 times or more.

| | Treatment | NIH-TrkA % Protection | NIH-TrkC % Protection | NIH wt % Protection |
|---|---|---|---|---|
| 4 | 10 μM P27 | 5 ± 2 | 13 ± 3 | −2 ± 4 |
| 5 | 10 μM P27 + 10 pM NT-3 | 4 ± 1 | 62 ± 6 | 5 ± 4 |
| 6 | 10 μM P23 | 15 ± 2 | 8 ± 2 | 0 ± 3 |
| 7 | 10 μM P23 + 10 pM NT-3 | 21 ± 3 | 51 ± 7 | 1 ± 3 |

TABLE 9

TrkA antagonistic activity of examples of preferred embodiments
NIH3T3 fibroblasts transfected with and expressing TrkA were treated
with the indicated ligands for a total of 72 hours. TrkA-expressing cells
respond optimally to 1 nM NGF and suboptimally to 10 nM NGF.
Survival was measured by MTT assays. % Protection was calculated as in
Table 4. Shown is the O.D. from one experiment, mean ± sem,
n = 4. Each experiment was repeated 3 times or more.

| | Treatment | NIH-TrkA % Protection | NIH wt % Protection |
|---|---|---|---|
| 1 | untreated | 0 ± 5 | 0 ± 4 |
| 2 | 1 nM NGF | 100 ± 4 | 4 ± 6 |
| 3 | 10 pM NGF | 28 ± 5 | 3 ± 5 |
| 4 | 10 μM P42 | 5 ± 2 | 0 ± 3 |
| 5 | 10 μM P43 | 4 ± 3 | 2 ± 4 |
| 6 | 1 nM NGF + 10 μM P42 | 68 ± 5 | nd |
| 7 | 10 pM NGF + 10 μM P42 | 9 ± 4 | nd |
| 8 | 1 nM NGF + 10 μM P43 | 55 ± 7 | nd |
| 9 | 10 pM NGF + 10 μM P43 | 12 ± 3 | nd |

Nd: not done

Further Considerations

The molecular nature of NT-3/TrkC interactions is important for the following reasons. Many protein-protein interactions occur via contact at a few key regions, "hot spots", rather than extensive interactions over the whole protein surface. These generally involve 10–30 contact side chains on discontinuous portions of each primary sequence. However, a relatively small fraction of these side chains are required for tight binding at the interfaces. Small molecules that interact with hot spots can interfere with the normal protein-protein interactions making the concept of hormone mimicry viable.

Previous results provide evidence that the turn regions of the neurotrophin NGF are hot-spots for the NGF/TrkA interaction (LeSauteur et al, 1995). NGF is a 22 kDa protein, which exists and functions as a dimer. It is highly conserved across species. Mature NT-3 shares 50 identical amino acids with NGF, mostly focused in regions that promote the common tertiary structure (eg all six Cys residues of the cysteine knot are conserved). The dimer interface region is composed of β-strands that maintains the conformation and disposition of structural motifs; these hydrophobic core residues are highly conserved amongst all neurotrophins. Conversely, the turn regions are highly variable, and appear to determine receptor-binding specificity.

The strong structural similarities between NGF and NT-3 (in the BDNF heterodimer) indicate the turn regions of NT-3 highlighted in FIG. 4 are important in docking of NT-3 with TrkC. Additionally mimics of the turn regions of NT-3 may also bind TrkA and p75 (as NT-3 does)

The data from studies of chimeric proteins is as follows. One NT-3 chimera that expresses NGF residues 1–66 and 115–122 (numbering according to NGF) exhibits gain of NGF-like function, with full retention of NT-3 activity. These findings imply the sequences that confer NT-3 like properties are contained within the region that corresponds to NGF residues 67–114. Another NT-3 chimera studied contained the NGF sequences at the N-terminus and at β-loop 3 region (ca residues 91–98). This recombinant had enhanced NGF function and diminished NT-3 activity relative to wild type NT-3. These data imply that a major contribution towards NT-3 binding and activity is attributable to β-loop 3. This is consistent with the studies of the first chimera because the β-loop 3 is within the region corresponding to residues 67–114 that was found to contain key regions for binding. Another study of NT-3/NGF chimeric proteins found that β-loop 3 was a critical region for determining specificity, and that proximal Arg and Tyr residues may enhance the binding.

Mutagenesis experiments reveal scattered residues of NT-3 that contribute to binding. Thus some loss of NT-3/TrkC affinity and loss of activity is seen upon substitution of six residues of NT-3 with the corresponding residues in NGF (S73D, F86Y, K88R, F101W, A107S, and V111A). These amino acids are discontinuous in the primary sequence, but they are proximal to β-loop 3 in the folded dimeric neurotrophin. Next to the β-loop 3 of NT-3 there is an arginine that is conserved between NGF and NT-3 but seems to play a different role in each neurotrophin. Significant loss of NT-3 bioactivity was seen in an NT-3 R103A mutant; however, no loss of NGF bioactivity was observed in a NGF R103A mutant. This is indicative of differences in the way these neurotrophins bind to their receptors. Moreover, adjacent to R103, there is a phenylalanine (F104) in NGF and a tryptophan (W104) in NT-3. These hydrophobic residues are solvent exposed and their substitution also leads to decreased bioactivity, suggesting a role either in binding or in stabilizing an active conformation.

It appears that the N-termini of the neurotrophins may play an important role in binding to their receptors. This region is a more difficult target for mimicry because the N-terminus of NT-3 (and that of NGF) is "unstructured" in solution and in the solid state. Modeling indicates that the N-terminus is composed of two subdomains comprising residues 1–8 and residues 9–11. Residues 1–8 are flexible, but 9–11 are rigid and maintain an electrostatic interaction between E(11) and R(118). Consequently, a long fold locates residues 1–8 near -loop 2/-loop 3.

NGF/p75 and NT-3/p75 interactions are at least partially mediated by β-loop 1 of the neurotrophin which features positively charged amino acids. They may also involve amino acids R114 and K115. Overall, these residues are discontinuous with the -loop 1 primary sequence, but are packed closely to it in the 3-D structure.

On the basis of the data above, it is appropriate to specifically incorporate one or more of the residues found in neurotrophins at positions 1–11; 29–34; 42–48; and 91–98. These will be the primary targets for lead discovery.

Table 10 provides sequence alignments.

TABLE 10

Alignment of amino acid sequences of mature neurotrophins in regions predicted to convey receptor binding and specificity.

| | region/domain | | | |
|---|---|---|---|---|
| | N-terminus | β-loop 1 | β-loop 2 | β-loop 3 |
| NGF | | | | |
| mouse | S STHPVFH (SEQ ID NO:1) | TATDIKGKEVT (SEQ ID NO:2) | EVNINNSVF (SEQ ID NO:9) | RQLTTDE KQAAWRF (SEQ ID NO:10) |
| rat | S STHPVFH (SEQ ID NO:1) | TATDIKGKEVT (SEQ ID NO:2) | EVNINNSVF (SEQ ID NO:9) | KQLTTDD KQAAWRF (SEQ ID NO:11) |
| human | SSS HPIFH (SEQ ID NO:3) | TATDIKGKEVM (SEQ ID NO:4) | EVNINNSVF (SEQ ID NO:9) | KQLTMDG KQAAWRF (SEQ ID NO:12) |
| NT-3 | | | | |
| rat | Y AEHKS H (SEQ ID NO:5) | SAIDIRGHQVT (SEQ ID NO:6) | EIKTGNSPV (SEQ ID NO:13) | KQLTSENNKLVGWRW (SEQ ID NO:14) |
| human | Y AEHKS H (SEQ ID NO:5) | SAIDIRGHQVT (SEQ ID NO:6) | EIKTGNSPV (SEQ ID NO:13) | KQLTSENNKLVGWRW (SEQ ID NO:14) |
| BDNF | | | | |
| human | HSDPARRGE (SEQ ID NO:7) | TAVDMSGGTHS (SEQ ID NO:8) | EKVPVSKGQ (SEQ ID NO:15) | RALTMDSKKRIGWRF (SEQ ID NO:16) |

| Abbreviations |
|---|
| BDNF, Brain Derived Neurotrophic Factor |
| BOC, tert-butoxycarbonyl |
| ChAT, Choline Acetyl Transferase |
| DMF, dimethylformamide |
| DRG: dorsal root ganglia |
| ELISA: enzyme-linked immunosorbent assay |
| FACScan, Fluorescent Activated Cell Scanner |
| FITC, fluorescein isothiocyanate |
| FMOC, fluorenyloxycarbonyl |
| MCF, mean channel fluorescence |
| MTT, 3(4,5-Dimethylthiazolyl-2)-2,5-diphenyl tetrazolium bromide |
| NGF, nerve growth factor |
| NT-3, neurotrophin-3 |
| RIA: radioimmunoassay |
| TFA, trifluoroacetic acid |
| Trt, trityl |

REFERENCES

Beglova, N, LeSauteur, L, Saragovi, H, and Gehring, K B (1998) Solution structure and internal motion of a bioactive peptide derived from Nerve Growth Factor. *J. Biol. Chem.* 273:23652–23658.

Feng, Y, Wang, Z, Jin, S, and Burgess, K (1998) SNAr Cyclizations To Form Cyclic Peptidomimetics of beta-turns. *J. Am. Chem. Soc.* 120:10768–9.

LeSauteur, L, Maliartchouk, S, Jeune, H L, Quirion, R, and Saragovi, H U (1996) Potent Human p140-TrkA Agonists Derived from an Anti-receptor Antibody. *J. Neurosci.* 16:1308–16.

LeSauteur, L, Wei, L, Gibbs, B, and Saragovi, H U (1995) Small Peptide Mimics of Nerve Growth Factor Bind TrkA Receptors and Affect Biological Responses. *J. Biol. Chem.* 270:6564–9.

Perez, P, Coll, P M, Hempstead, B L, Martin-Zanca, D, and Chao, M V (1995) NGF Binding to the Trk Tyrosine Kinase Receptor Requires the Extracellular Immunoglobulin-like Domains. *Mol. Cell. Neurosci.* 6:97–105.

Saragovi, H U, and Burgess, K (1999) Small molecule and protein-based neurotrophic ligands: agonists and antagonists as therapeutic agents. *Expert Opinion in Therapeutic Patents* 9:737–751.

Saragovi, H U, Zheng, W H, Maliartchouk, S, DiGugliemo, G M, Mawal, Y R, Kamen, A, Woo, S B, Cuello, A C, Debeir, T, and Neet, K E (1998) A TrkA selective, fast internalizing Nerve Growth Factor-antibody complex induces trophic but not neuritogenic signals. *J. Biol. Chem.* 274:34933–34940.

What is claimed is:
1. A method of treating or preventing a neurotrophin receptor mediated disorder in a patient comprising administering to a patient in need, an acceptable neurotrophin receptor agonistic or antagonistic amount of a neurotrophin mimicking β-turn peptidomimetic cyclic compound having a macrocyclic ring of 13 to 17 carbon atoms.

2. A method according to claim 1, wherein said compound has one or more side chains on said macrocyclic ring, which one or more side chains extend from backbone ring atoms.

3. A method according to claim 2, wherein said one or more side chains correspond to residues found within β-turns of a neurotrophin.

4. A method according to claim 3, wherein said neurotrophin is nerve growth factor (NGF), neurotrophin-3 (NT-3), neurotrophin-4/5 (NT4/5), or brain derived neurotrophic factor (BDNF).

5. A method according to claim 3, wherein said neurotrophin binds to a receptor.

6. A method according to claim 3, wherein said neurotrophin receptor is TrkA, TrkB, TrkC or p75.

7. A method according to claim 1, wherein said macrocyclic ring has 14 ring atoms.

8. A method according to claim 1, wherein said macrocyclic ring has 15 ring atoms.

9. A method according to claim 1, wherein said macrocyclic ring has 16 ring atoms.

10. A method according to claim 1, wherein said cyclic compound is a β-turn peptidomimetic cyclic compound of formula (I)

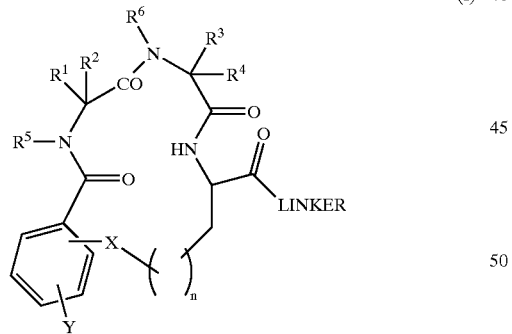

wherein $R^1$ and $R^3$ are selected from hydrogen, alkyl or aryl substituents found in a natural or unnatural amino acid;
$R^2$ and $R^4$ are hydrogen or alkyl;
$R^5$ and $R^6$ are hydrogen;
$R^1$ and $R^2$ or $R^3$ and $R^4$ together with the carbon atom to which they are attached form a cyclopropyl, cyclobutyl, cyclopentyl or cyclohexyl group;
Y is hydrogen or one or two aromatic substituents;
X is selected from O, N, S, P, Se, C, alkylene of 1 to 6 carbon atoms, SO, $SO_2$ or NH;
N is 0, 1, 2, 3, 4 or 5; and
LINKER is a linking group effective to form dimers of the compound of formula (I) by reaction with a homo bifunctional compound.

11. A method according to claim 10, wherein X is O, S or NH, $R^1$, $R^3$, $R^5$ and $R^6$ are each hydrogen atoms and the macrocyclic ring has 14, 15 or 16 ring atoms.

12. A method according to claim 10, wherein $R^1$ and $R^3$ are derived from a sequence of different amino acids side chains selected from natural and synthetic amino acids.

13. A method according to claim 10, wherein X is —O—, —S— or —NH—.

14. A method according to claim 1, wherein said compound is selected from

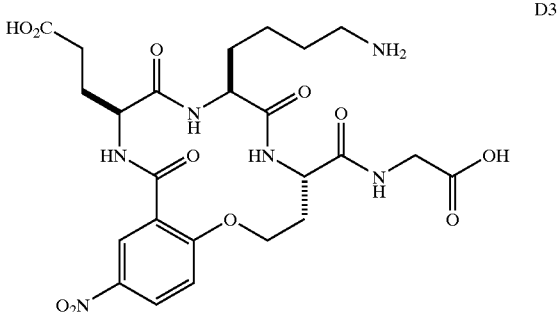

D3

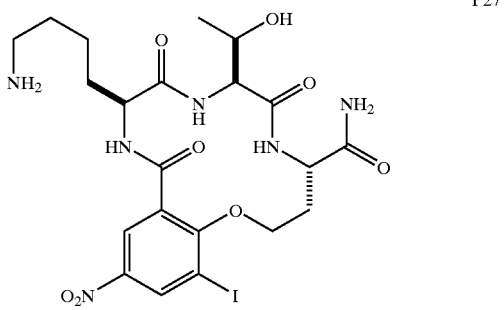

P27

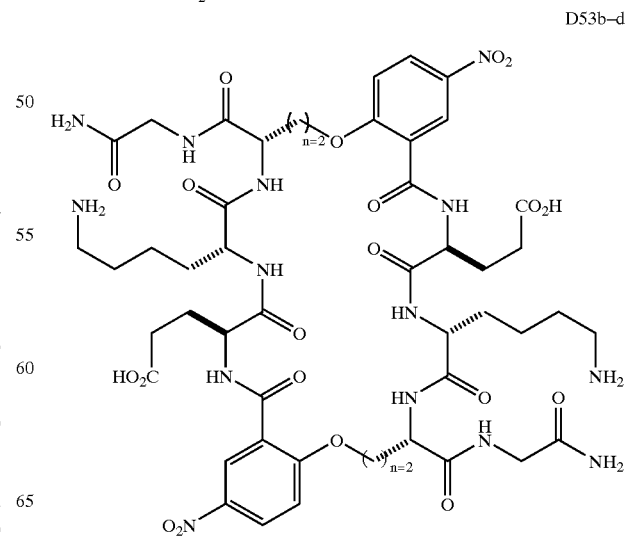

D53b–d

25
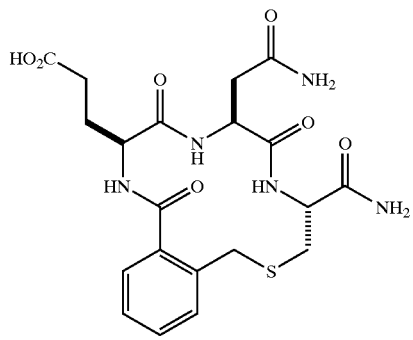
P56
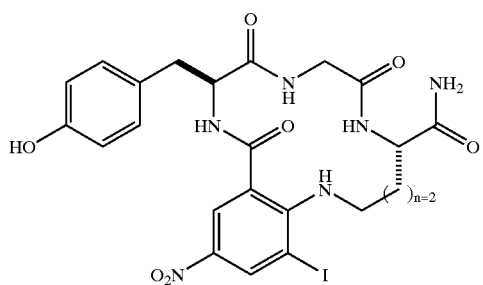
P57
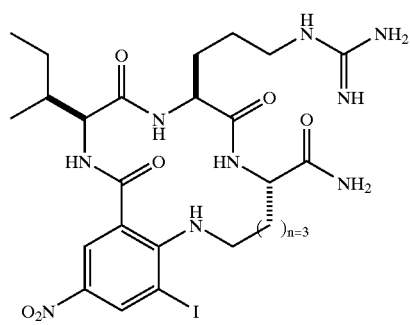
P58
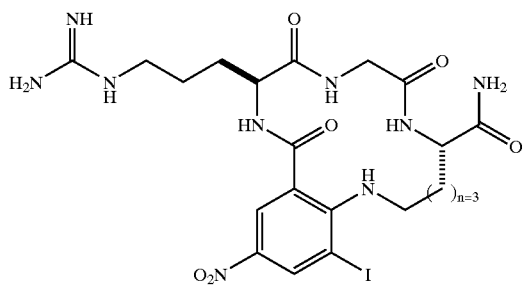
P42
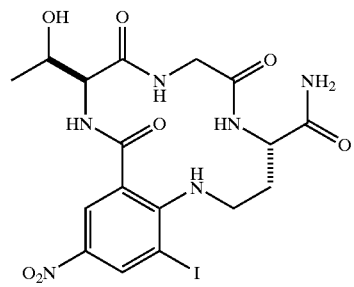
P43
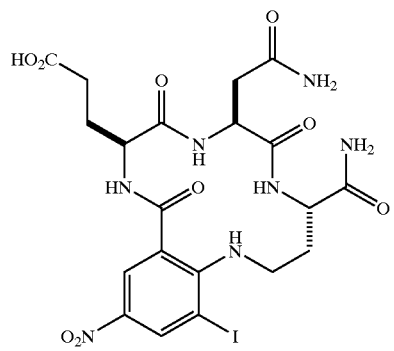
P39
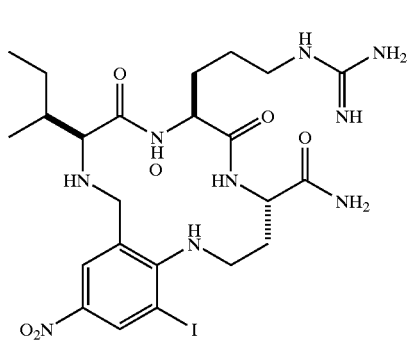
D21
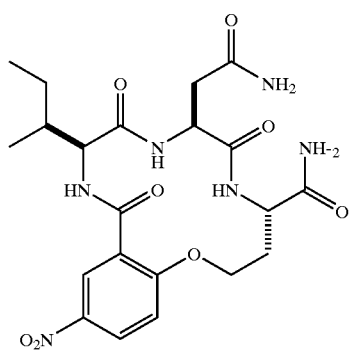
D46
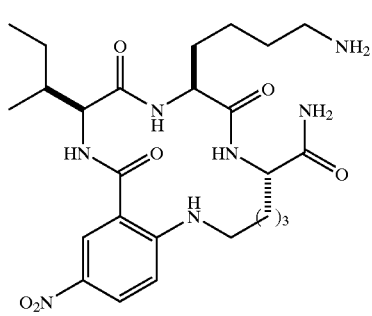

-continued
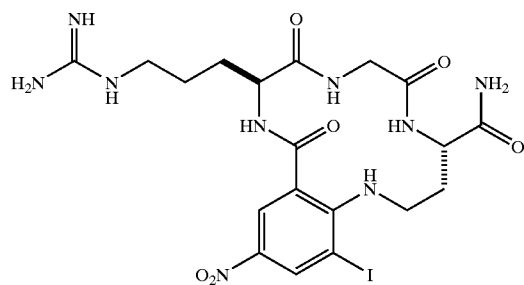
P40
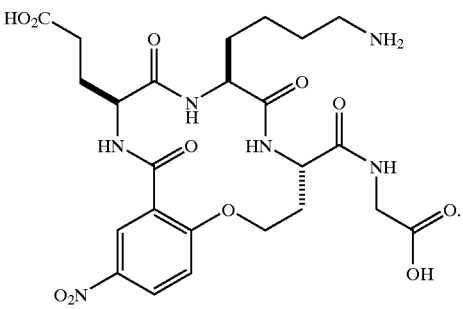
D3
16. A method according to claim 1, wherein said compound is the compound of formula
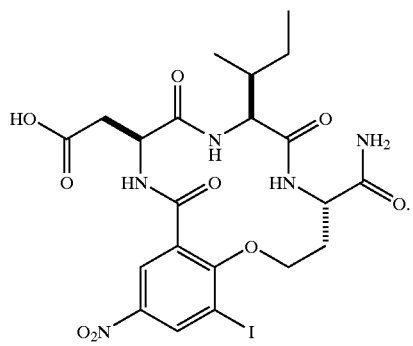
P23
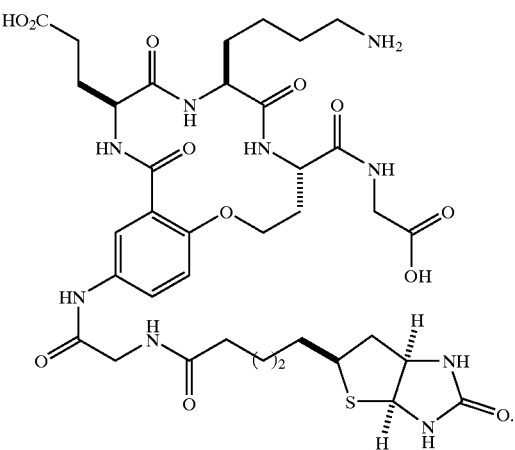
15. A method according to claim 1, wherein said compound is the compound of formula
* * * * *

UNITED STATES PATENT AND TRADEMARK OFFICE
CERTIFICATE OF CORRECTION

| | | |
|---|---|---|
| PATENT NO. | : 6,881,719 B2 | Page 1 of 1 |
| APPLICATION NO. | : 10/181546 | |
| DATED | : April 19, 2005 | |
| INVENTOR(S) | : Horacio Uri Saragovi et al. | |

It is certified that error appears in the above-identified patent and that said Letters Patent is hereby corrected as shown below:

Claim 1, column 47, line 17;
  "a macrocyclic ring of 13 to 17 carbon atoms".
Should read –
  "a macrocyclic ring of 13 to 17 atoms".

Signed and Sealed this
Nineteenth Day of April, 2011

David J. Kappos
*Director of the United States Patent and Trademark Office*